United States Patent
Johnston et al.

(10) Patent No.: US 7,736,380 B2
(45) Date of Patent: Jun. 15, 2010

(54) CERVICAL PLATE SYSTEM

(75) Inventors: Terry Johnston, Redwood City, CA (US); Fred Geisler, Aurora, IL (US)

(73) Assignee: Rhausler, Inc., San Carlos, CA (US)

( * ) Notice: Subject to any disclaimer, the term of this patent is extended or adjusted under 35 U.S.C. 154(b) by 1031 days.

(21) Appl. No.: 11/313,317

(22) Filed: Dec. 21, 2005

(65) Prior Publication Data

US 2006/0167456 A1 Jul. 27, 2006

Related U.S. Application Data

(60) Provisional application No. 60/637,690, filed on Dec. 21, 2004.

(51) Int. Cl.
*A61B 17/56* (2006.01)
*A61B 17/58* (2006.01)
*A61B 17/60* (2006.01)
*A61B 17/84* (2006.01)
*A61B 17/80* (2006.01)
*A61B 17/86* (2006.01)
*A61B 17/88* (2006.01)

(52) U.S. Cl. ............... 606/280; 606/86; 606/87; 606/96; 606/98; 606/281; 606/323; 606/902; 606/903; 606/904; 606/905; 606/906; 606/915

(58) Field of Classification Search ............ 606/86, 606/87, 96, 98, 280, 281, 323, 902–906, 606/915
See application file for complete search history.

(56) References Cited

U.S. PATENT DOCUMENTS 74,489 A 2/1868 Bidwell (Continued)

FOREIGN PATENT DOCUMENTS

AU 756121 3/2002

(Continued)

OTHER PUBLICATIONS

John D. Clausen, Biomechanical Evaluation of Caspar and Cervical Spine Locking Plate Systems in a Cadaveric Model, Journal of Neurosurgery, Jun. 1996, pp. 1039-1045, vol. 84.

(Continued)

*Primary Examiner*—Thomas C Barrett
*Assistant Examiner*—Sameh Boles
(74) *Attorney, Agent, or Firm*—Kramer & Amado P.C.

(57) ABSTRACT

A device, system and method for securing a plate to a bone. An anchor device has a screw (with a head portion) and a locking disc. The head portion includes a slotted wall defining a plurality of petals disposed around a central opening. The screw further includes an internal bore. The locking disc is rotatably disposed within the central opening, such that in a first rotational position the petals may flex inwardly, and in a second rotational position the petals are substantially prevented from flexing inwardly. A tool for manipulating the anchor device has a shaft with its end configured to mate with the internal bore of the screw to permit selective rotation of the screw, and a sleeve member rotatably and slideably mounted on the shaft having an end that mates with the locking disc to permit selective rotation of the disc.

56 Claims, 9 Drawing Sheets

U.S. PATENT DOCUMENTS

| | | |
|---|---|---|
| 90,132 A | 5/1869 | Stamper |
| 824,867 A | 7/1906 | Houghton |
| 1,105,105 A | 7/1914 | Sherman |
| 1,501,222 A | 7/1924 | Lamp |
| 1,501,422 A | 7/1924 | Strout |
| 1,980,336 A | 11/1934 | Hoagland |
| 2,250,417 A | 7/1941 | Ettinger |
| 2,372,866 A | 4/1945 | Tofflemire |
| 2,391,537 A | 12/1945 | Anderson |
| 2,391,693 A | 12/1945 | Ettinger |
| 2,393,694 A | 1/1946 | Kirschner |
| 2,406,987 A | 9/1946 | Anderson |
| 2,423,511 A | 7/1947 | Luben et al. |
| 2,497,626 A | 2/1950 | Persall |
| 2,757,457 A | 8/1956 | Ziegelski, Sr. |
| 2,780,522 A | 2/1957 | Gloss et al. |
| 2,780,830 A | 2/1957 | Kammerer, Jr. |
| 2,832,390 A | 4/1958 | Kustusth |
| 3,244,170 A | 4/1966 | McElvenny |
| 3,386,437 A | 6/1968 | Treace |
| 3,552,389 A | 1/1971 | Allgower et al. |
| 3,604,414 A | 9/1971 | Borges |
| 3,709,219 A | 1/1973 | Halloran |
| 3,741,205 A | 6/1973 | Markolf et al. |
| 3,750,652 A | 8/1973 | Sherwin |
| 3,837,522 A | 9/1974 | Lesnansky, Jr. |
| 3,840,014 A | 10/1974 | Ling et al. |
| 3,842,825 A | 10/1974 | Wagner |
| RE28,841 E | 6/1976 | Allgower et al. |
| 3,960,147 A | 6/1976 | Murray |
| 4,069,586 A | 1/1978 | Skelton |
| 4,102,339 A | 7/1978 | Weber et al. |
| 4,113,227 A | 9/1978 | Cigliano |
| 4,135,505 A | 1/1979 | Day |
| 4,220,146 A | 9/1980 | Cloutier |
| 4,257,409 A | 3/1981 | Bacal et al. |
| 4,328,721 A | 5/1982 | Massari |
| 4,338,926 A | 7/1982 | Kummer et al. |
| 4,349,017 A | 9/1982 | Sayegh |
| RE31,628 E | 7/1984 | Allgower et al. |
| 4,483,334 A | 11/1984 | Murray |
| 4,484,570 A | 11/1984 | Sutter et al. |
| 4,488,462 A | 12/1984 | Wall |
| 4,488,543 A | 12/1984 | Tornier |
| 4,493,317 A | 1/1985 | Klane |
| 4,503,848 A | 3/1985 | Caspar et al. |
| 4,542,539 A | 9/1985 | Rowe, Jr. et al. |
| 556,645 A | 3/1986 | Reesing |
| 4,611,580 A | 9/1986 | Wu |
| 4,620,533 A | 11/1986 | Mears |
| 4,648,388 A | 3/1987 | Steffee |
| 4,651,724 A | 3/1987 | Berentey et al. |
| 4,719,905 A | 1/1988 | Steffee |
| 4,733,657 A | 3/1988 | Kluger |
| 4,743,256 A | 5/1988 | Brantigan |
| 4,776,330 A | 10/1988 | Chapman et al. |
| 4,790,297 A | 12/1988 | Luque |
| 4,794,918 A | 1/1989 | Wolter |
| 4,834,757 A | 5/1989 | Brantigan |
| 4,836,196 A | 6/1989 | Park et al. |
| 4,840,525 A | 6/1989 | Rebentisch |
| 4,878,915 A | 11/1989 | Brantigan |
| 4,890,631 A | 1/1990 | Hardy |
| 4,896,661 A | 1/1990 | Bogert et al. |
| 4,898,161 A | 2/1990 | Grundei |
| 4,907,927 A | 3/1990 | Choiniere |
| 4,913,134 A | 4/1990 | Luque |
| 4,957,495 A | 9/1990 | Kluger |
| 4,957,496 A | 9/1990 | Schmidt |
| 4,959,065 A | 9/1990 | Arnett et al. |
| 5,000,165 A | 3/1991 | Watanabe |
| 5,000,166 A | 3/1991 | Karpf |
| 5,002,542 A | 3/1991 | Frigg |
| 5,005,562 A | 4/1991 | Cotrel |
| 5,009,661 A | 4/1991 | Michelson |
| 5,015,247 A | 5/1991 | Michelson |
| 5,019,079 A | 5/1991 | Ross |
| 5,024,213 A | 6/1991 | Asher et al. |
| D318,118 S | 7/1991 | Michelson |
| 5,030,220 A | 7/1991 | Howland |
| 5,041,113 A | 8/1991 | Biedermann et al. |
| 5,041,114 A | 8/1991 | Chapman et al. |
| 5,052,373 A | 10/1991 | Michelson |
| 5,053,034 A | 10/1991 | Olerud |
| 5,053,036 A | 10/1991 | Perren et al. |
| 5,057,111 A | 10/1991 | Park |
| 5,059,194 A | 10/1991 | Michelson |
| 5,084,048 A | 1/1992 | Jacob et al. |
| 5,084,049 A | 1/1992 | Asher et al. |
| D324,424 S | 3/1992 | Michelson |
| 5,102,412 A | 4/1992 | Rogozinski |
| 5,120,171 A | 6/1992 | Lasner |
| 5,122,131 A | 6/1992 | Tsou |
| 5,127,912 A | 7/1992 | Ray et al. |
| 5,129,899 A | 7/1992 | Small et al. |
| 5,129,900 A | 7/1992 | Asher et al. |
| 5,147,360 A | 9/1992 | Bebousset |
| 5,147,361 A | 9/1992 | Ojima et al. |
| 5,151,103 A | 9/1992 | Tepic et al. |
| 5,167,662 A | 12/1992 | Hayes et al. |
| 5,169,270 A | 12/1992 | Erickson |
| 5,171,279 A | 12/1992 | Mathews |
| 5,176,678 A | 1/1993 | Tsou |
| 5,180,381 A | 1/1993 | Aust et al. |
| 5,190,544 A | 3/1993 | Chapman et al. |
| 5,209,751 A | 5/1993 | Farris et al. |
| 5,217,497 A | 6/1993 | Mehdian |
| 5,222,954 A | 6/1993 | Baker et al. |
| 5,226,766 A | 7/1993 | Lasner |
| 5,234,430 A | 8/1993 | Huebner |
| 5,234,431 A | 8/1993 | Keller |
| 5,242,443 A | 9/1993 | Kambin |
| 5,254,118 A | 10/1993 | Mirkovic |
| 5,261,910 A | 11/1993 | Warden et al. |
| 5,275,600 A | 1/1994 | Allard et al. |
| 5,282,862 A | 2/1994 | Baker et al. |
| 5,300,073 A | 4/1994 | Ray et al. |
| 5,306,275 A | 4/1994 | Bryan |
| 5,312,404 A | 5/1994 | Asher et al. |
| 5,312,405 A | 5/1994 | Korotko et al. |
| 5,324,295 A | 6/1994 | Shapiro |
| 5,330,477 A | 7/1994 | Crook |
| 5,334,203 A | 8/1994 | Wagner |
| 5,338,197 A | 8/1994 | Kwan |
| 5,344,422 A | 9/1994 | Frigg |
| 5,352,225 A | 10/1994 | Yuan et al. |
| 5,352,226 A | 10/1994 | Lin |
| 5,360,429 A | 11/1994 | Jeanson et al. |
| 5,364,398 A | 11/1994 | Chapman et al. |
| 5,364,399 A | 11/1994 | Lowery et al. |
| 5,368,594 A | 11/1994 | Martin et al. |
| 5,378,384 A | 1/1995 | Hopstock et al. |
| 5,380,323 A | 1/1995 | Howland |
| 5,380,325 A | 1/1995 | Lahille et al. |
| 5,380,328 A | 1/1995 | Morgan |
| 5,382,248 A | 1/1995 | Jacobson et al. |
| 5,393,161 A | 2/1995 | Mata et al. |
| 5,395,371 A | 3/1995 | Miller et al. |
| 5,397,363 A | 3/1995 | Gelbard |
| 5,403,314 A | 4/1995 | Currier |
| 5,405,391 A | 4/1995 | Hednerson et al. |
| 5,417,533 A | 5/1995 | Lasner |
| 5,423,826 A | 6/1995 | Coates et al. |
| 5,425,772 A | 6/1995 | Brantigan et al. |

| Patent | Kind | Date | Inventor |
|---|---|---|---|
| 5,437,674 | A | 8/1995 | Worcel et al. |
| 5,451,227 | A | 9/1995 | Michaelson |
| 5,456,685 | A | 10/1995 | Huebner |
| 5,468,241 | A | 11/1995 | Metz-Stavenhagen |
| 5,474,551 | A | 12/1995 | Finn et al. |
| 5,476,463 | A | 12/1995 | Boachie-Adjei et al. |
| 5,477,254 | A | 12/1995 | Stephens |
| 5,478,340 | A | 12/1995 | Kluger |
| 5,478,348 | A | 12/1995 | Bajada |
| 5,480,440 | A | 1/1996 | Kambin |
| 5,484,437 | A | 1/1996 | Michelson |
| 5,486,174 | A | 1/1996 | Fournet-Fayard et al. |
| 5,486,176 | A | 1/1996 | Hildebrand et al. |
| 5,487,742 | A | 1/1996 | Cotrel |
| 5,487,744 | A | 1/1996 | Howland |
| 5,492,442 | A | 2/1996 | Lasner |
| 5,496,321 | A | 3/1996 | Puno et al. |
| 5,498,262 | A | 3/1996 | Bryan |
| 5,498,264 | A | 3/1996 | Schlapfer et al. |
| 5,505,732 | A | 4/1996 | Michelson |
| 5,507,746 | A | 4/1996 | Lin |
| 5,514,132 | A | 5/1996 | Csernatony et al. |
| 5,520,690 | A | 5/1996 | Errico et al. |
| 5,522,816 | A | 6/1996 | Dinello et al. |
| 5,522,899 | A | 6/1996 | Michelson |
| 5,527,310 | A | 6/1996 | Cole et al. |
| 5,527,314 | A | 6/1996 | Brumfield et al. |
| 5,531,554 | A | 7/1996 | Jeanson et al. |
| 5,531,746 | A | 7/1996 | Errico et al. |
| 5,534,002 | A | 7/1996 | Brumfield et al. |
| 5,534,031 | A | 7/1996 | Matsuzaki et al. |
| 5,540,690 | A | 7/1996 | Miller et al. |
| 5,545,162 | A | 8/1996 | Huebner |
| 5,545,163 | A | 8/1996 | Miller et al. |
| 5,545,165 | A | 8/1996 | Biedermann et al. |
| 5,545,228 | A | 8/1996 | Kambin |
| 5,549,612 | A | 8/1996 | Yapp et al. |
| 5,558,674 | A | 9/1996 | Heggeness et al. |
| D374,283 | S | 10/1996 | Michelson |
| 5,562,661 | A | 10/1996 | Yoshimi et al. |
| 5,562,662 | A | 10/1996 | Brumfield et al. |
| 5,562,663 | A | 10/1996 | Wisnewski et al. |
| 5,562,672 | A | 10/1996 | Huebner et al. |
| 5,569,247 | A | 10/1996 | Morrison |
| 5,569,248 | A | 10/1996 | Mathews |
| 5,569,251 | A | 10/1996 | Baker et al. |
| 5,575,791 | A | 11/1996 | Lin |
| 5,578,034 | A | 11/1996 | Estes |
| D377,093 | S | 12/1996 | Michelson |
| D377,095 | S | 12/1996 | Michelson |
| D377,096 | S | 12/1996 | Michelson |
| 5,582,612 | A | 12/1996 | Lin |
| 5,584,831 | A | 12/1996 | McKay |
| 5,584,833 | A | 12/1996 | Fournet-Fayard et al. |
| 5,584,887 | A | 12/1996 | Kambin |
| 5,586,984 | A | 12/1996 | Errico et al. |
| D377,527 | S | 1/1997 | Michelson |
| 5,593,409 | A | 1/1997 | Michelson |
| 5,601,552 | A | 2/1997 | Cotrel |
| 5,601,553 | A | 2/1997 | Trebing et al. |
| 5,603,713 | A | 2/1997 | Aust et al. |
| 5,607,426 | A | 3/1997 | Ralph et al. |
| 5,609,592 | A | 3/1997 | Brumfield et al. |
| 5,609,635 | A | 3/1997 | Michelson |
| 5,613,968 | A | 3/1997 | Lin |
| 5,616,142 | A | 4/1997 | Yuan et al. |
| 5,616,144 | A | 4/1997 | Yapp et al. |
| 5,616,414 | A | 4/1997 | Hopstock et al. |
| 5,622,649 | A | 4/1997 | Hunter et al. |
| 5,624,440 | A | 4/1997 | Huebner |
| 5,624,442 | A | 4/1997 | Mellinger et al. |
| 5,626,956 | A | 5/1997 | Hopstock et al. |
| 5,643,265 | A | 7/1997 | Errico et al. |
| 5,645,544 | A | 7/1997 | Tai et al. |
| 5,647,873 | A | 7/1997 | Errico et al. |
| 5,651,789 | A | 7/1997 | Cotrel |
| 5,653,713 | A | 8/1997 | Michelson |
| 5,655,089 | A | 8/1997 | Bucci |
| 5,658,283 | A | 8/1997 | Huebner |
| 5,662,649 | A | 9/1997 | Huebner |
| 5,662,652 | A | 9/1997 | Schafer et al. |
| 5,665,087 | A | 9/1997 | Huebner |
| 5,665,089 | A | 9/1997 | Dall et al. |
| 5,667,507 | A | 9/1997 | Corin et al. |
| 5,669,911 | A | 9/1997 | Errico et al. |
| 5,672,175 | A | 9/1997 | Martin |
| 5,676,666 | A | 10/1997 | Oxland et al. |
| 5,676,703 | A | 10/1997 | Gelbard |
| 5,681,311 | A | 10/1997 | Foley et al. |
| 5,683,389 | A | 11/1997 | Orsak |
| 5,683,391 | A | 11/1997 | Boyd |
| 5,688,272 | A | 11/1997 | Montague et al. |
| 5,690,630 | A | 11/1997 | Errico et al. |
| 5,697,934 | A | 12/1997 | Huebner |
| 5,702,395 | A | 12/1997 | Hopf |
| 5,702,472 | A | 12/1997 | Huebner |
| 5,704,936 | A | 1/1998 | Mazel |
| 5,707,373 | A | 1/1998 | Sevrain et al. |
| 5,709,684 | A | 1/1998 | Errico et al. |
| 5,713,900 | A | 2/1998 | Benzel et al. |
| D392,387 | S | 3/1998 | Michelson |
| 5,725,527 | A | 3/1998 | Biedermann et al. |
| 5,725,588 | A | 3/1998 | Errico et al. |
| 5,728,097 | A | 3/1998 | Mathews |
| 5,729,097 | A | 3/1998 | Holzer |
| 5,735,853 | A | 4/1998 | Olerud |
| 5,735,899 | A | 4/1998 | Schwartz et al. |
| 5,741,253 | A | 4/1998 | Michelson |
| 5,743,907 | A | 4/1998 | Asher et al. |
| 5,743,911 | A | 4/1998 | Cotrel |
| 5,755,796 | A | 5/1998 | Ibo et al. |
| 5,766,252 | A | 6/1998 | Henry et al. |
| 5,766,254 | A | 6/1998 | Gelbard |
| 5,769,856 | A | 6/1998 | Dong et al. |
| 5,772,661 | A | 6/1998 | Michelson |
| 5,772,662 | A | 6/1998 | Chapman et al. |
| 5,776,196 | A | 7/1998 | Matsuzaki et al. |
| 5,776,199 | A | 7/1998 | Michelson |
| 5,785,710 | A | 7/1998 | Michelson |
| 5,785,711 | A | 7/1998 | Errico et al. |
| D397,436 | S | 8/1998 | Michelson |
| 5,792,044 | A | 8/1998 | Foley et al. |
| 5,797,909 | A | 8/1998 | Michelson |
| 5,810,819 | A | 9/1998 | Errico et al. |
| 5,810,824 | A | 9/1998 | Chan |
| 5,810,825 | A | 9/1998 | Huebner |
| 5,817,094 | A | 10/1998 | Errico et al. |
| 5,824,108 | A | 10/1998 | Huebner |
| D402,032 | S | 12/1998 | Stone |
| 5,849,012 | A | 12/1998 | Abboudi |
| D404,128 | S | 1/1999 | Huebner |
| 5,860,973 | A | 1/1999 | Michelson |
| D405,176 | S | 2/1999 | Michelson |
| 5,865,845 | A | 2/1999 | Thalgott |
| 5,868,789 | A | 2/1999 | Huebner |
| 5,871,486 | A | 2/1999 | Huebner et al. |
| D406,646 | S | 3/1999 | Stone |
| 5,876,402 | A | 3/1999 | Errico et al. |
| 5,876,446 | A | 3/1999 | Agrawal et al. |
| 5,882,350 | A | 3/1999 | Ralph et al. |
| 5,888,204 | A | 3/1999 | Ralph et al. |
| 5,888,221 | A | 3/1999 | Gelbard |
| 5,899,903 | A | 5/1999 | Cotrel |
| 5,902,231 | A | 5/1999 | Foley et al. |
| 5,921,985 | A | 7/1999 | Ross, Jr. et al. |
| 5,938,663 | A | 8/1999 | Petreto |

| | | | | | | |
|---|---|---|---|---|---|---|
| 5,944,721 | A | 8/1999 | Huebner | 6,206,890 B1 | 3/2001 | Truwit |
| 5,947,965 | A | 9/1999 | Bryan | D440,311 S | 4/2001 | Michelson |
| 5,947,966 | A | 9/1999 | Drewry et al. | 6,210,412 B1 | 4/2001 | Michelson |
| 5,951,558 | A | 9/1999 | Fiz | 6,217,509 B1 | 4/2001 | Foley et al. |
| 5,954,635 | A | 9/1999 | Foley et al. | RE37,161 E | 5/2001 | Michelson |
| 5,954,722 | A | 9/1999 | Bono | 6,224,602 B1 | 5/2001 | Hayes |
| 5,957,953 | A | 9/1999 | DiPoto et al. | 6,224,607 B1 | 5/2001 | Michelson |
| 5,961,518 | A | 10/1999 | Errico et al. | 6,231,610 B1 | 5/2001 | Geisler |
| 5,961,555 | A | 10/1999 | Huebner | 6,234,705 B1 | 5/2001 | Troxell |
| 5,964,762 | A | 10/1999 | Biedermann et al. | 6,235,033 B1 | 5/2001 | Brace et al. |
| 5,964,768 | A | 10/1999 | Huebner | 6,235,034 B1 * | 5/2001 | Bray ............................ 606/71 |
| 5,976,134 | A | 11/1999 | Huebner | 6,241,731 B1 | 6/2001 | Fiz |
| 5,980,521 | A | 11/1999 | Montague et al. | 6,241,770 B1 | 6/2001 | Michelson |
| 5,984,922 | A | 11/1999 | McKay | 6,258,089 B1 | 7/2001 | Campbell et al. |
| 5,984,924 | A | 11/1999 | Asher et al. | 6,258,091 B1 | 7/2001 | Sevrain et al. |
| 5,993,463 | A | 11/1999 | Truwit | 6,261,291 B1 | 7/2001 | Talaber et al. |
| 5,997,539 | A | 12/1999 | Errico et al. | 6,264,656 B1 | 7/2001 | Michelson |
| 6,001,099 | A | 12/1999 | Huebner | 6,267,765 B1 | 7/2001 | Taylor et al. |
| 6,004,322 | A | 12/1999 | Bernstein | 6,267,770 B1 | 7/2001 | Truwit |
| 6,007,487 | A | 12/1999 | Foley et al. | 6,270,498 B1 | 8/2001 | Michelson |
| 6,017,344 | A | 1/2000 | Errico et al. | 6,280,445 B1 | 8/2001 | Morrison et al. |
| 6,017,345 | A | 1/2000 | Richelsoph | 6,283,967 B1 | 9/2001 | Troxell et al. |
| 6,017,347 | A | 1/2000 | Huebner et al. | 6,287,309 B1 | 9/2001 | Baccelli et al. |
| 6,022,350 | A | 2/2000 | Ganem | 6,290,703 B1 | 9/2001 | Ganem |
| 6,030,162 | A | 2/2000 | Huebner | D449,692 S | 10/2001 | Michelson |
| 6,030,388 | A | 2/2000 | Yoshimi et al. | 6,299,614 B1 | 10/2001 | Kretschmer et al. |
| 6,030,389 | A | 2/2000 | Wagner et al. | 6,299,615 B1 | 10/2001 | Huebner |
| 6,032,309 | A | 3/2000 | Michelson | 6,302,914 B1 | 10/2001 | Michelson |
| D425,989 | S | 5/2000 | Michelson | 6,306,137 B2 | 10/2001 | Troxell |
| 6,066,175 | A | 5/2000 | Henderson et al. | 6,306,139 B1 | 10/2001 | Fuentes |
| 6,077,271 | A | 6/2000 | Huebner et al. | 6,315,779 B1 | 11/2001 | Morrison et al. |
| 6,080,155 | A | 6/2000 | Michelson | 6,331,179 B1 | 12/2001 | Freid et al. |
| 6,080,156 | A | 6/2000 | Asher et al. | 6,342,055 B1 | 1/2002 | Eisermann et al. |
| 6,083,226 | A | 7/2000 | Fiz | 6,350,283 B1 | 2/2002 | Michelson |
| 6,083,228 | A | 7/2000 | Michelson | RE37,665 E | 4/2002 | Ralph et al. |
| 6,090,111 | A | 7/2000 | Nichols | 6,364,880 B1 | 4/2002 | Michelson |
| 6,096,038 | A | 8/2000 | Michelson | 6,368,329 B1 | 4/2002 | Truwit |
| 6,102,953 | A | 8/2000 | Huebner | 6,379,357 B1 | 4/2002 | Bernstein et al. |
| 6,113,600 | A | 9/2000 | Drummond et al. | 6,383,186 B1 | 5/2002 | Michelson |
| 6,117,173 | A | 9/2000 | Taddia et al. | 6,398,783 B1 | 6/2002 | Michelson |
| 6,120,502 | A | 9/2000 | Michelson | 6,402,751 B1 | 6/2002 | Hoeck et al. |
| 6,120,503 | A | 9/2000 | Michelson | 6,402,752 B2 | 6/2002 | Schaffler-Wachter et al. |
| 6,120,505 | A | 9/2000 | Huebner | 6,413,258 B1 | 7/2002 | Bernhardt, Jr. |
| 6,123,705 | A | 9/2000 | Michelson | 6,413,259 B1 | 7/2002 | Lyons et al. |
| 6,123,706 | A | 9/2000 | Lange | 6,416,528 B1 | 7/2002 | Michelson |
| 6,129,740 | A | 10/2000 | Michelson | 6,423,064 B1 | 7/2002 | Kluger |
| 6,136,001 | A | 10/2000 | Michelson | 6,423,067 B1 | 7/2002 | Eisermann |
| 6,136,003 | A | 10/2000 | Hoeck et al. | 6,425,859 B1 | 7/2002 | Foley et al. |
| 6,139,550 | A | 10/2000 | Michelson | 6,428,542 B1 | 8/2002 | Michelson |
| 6,139,551 | A | 10/2000 | Michelson | 6,432,108 B1 | 8/2002 | Burgess et al. |
| D433,506 | S | 11/2000 | Asfora | 6,436,098 B1 | 8/2002 | Michelson |
| 6,142,997 | A | 11/2000 | Michelson | 6,436,100 B1 | 8/2002 | Berger |
| 6,146,383 | A | 11/2000 | Studer et al. | 6,440,139 B2 | 8/2002 | Michelson |
| 6,149,650 | A | 11/2000 | Michelson | 6,447,544 B1 | 9/2002 | Michelson |
| 6,149,653 | A | 11/2000 | Deslauriers | 6,447,547 B1 | 9/2002 | Michelson |
| 6,152,871 | A | 11/2000 | Foley et al. | 6,454,769 B2 | 9/2002 | Wagner et al. |
| 6,152,927 | A | 11/2000 | Farris et al. | 6,454,771 B1 | 9/2002 | Michelson |
| RE37,005 | E | 12/2000 | Michelson | 6,458,133 B1 | 10/2002 | Lin |
| 6,159,214 | A | 12/2000 | Michelson | 6,468,276 B1 | 10/2002 | McKay |
| 6,162,170 | A | 12/2000 | Foley et al. | 6,478,823 B1 | 11/2002 | Michelson |
| 6,162,224 | A | 12/2000 | Huebner | 6,482,207 B1 | 11/2002 | Errico |
| 6,168,627 | B1 | 1/2001 | Huebner | 6,485,517 B1 | 11/2002 | Michelson |
| 6,168,628 | B1 | 1/2001 | Huebner | 6,491,694 B1 | 12/2002 | Orsak |
| 6,171,309 | B1 | 1/2001 | Huebner | 6,494,913 B1 | 12/2002 | Huebner |
| 6,176,823 | B1 | 1/2001 | Foley et al. | 6,500,205 B1 | 12/2002 | Michelson |
| 6,176,861 | B1 | 1/2001 | Bernstein et al. | 6,503,250 B2 | 1/2003 | Paul |
| 6,179,838 | B1 | 1/2001 | Fiz | 6,508,818 B2 | 1/2003 | Steiner et al. |
| 6,190,388 | B1 | 2/2001 | Michelson | 6,517,544 B1 | 2/2003 | Michelson |
| 6,193,721 | B1 | 2/2001 | Michelson | 6,520,907 B1 | 2/2003 | Foley et al. |
| 6,193,758 | B1 | 2/2001 | Huebner | 6,520,990 B1 | 2/2003 | Ray |
| 6,197,028 | B1 | 3/2001 | Ray et al. | 6,527,776 B1 | 3/2003 | Michelson |
| 6,200,320 | B1 | 3/2001 | Michelson | 6,533,786 B1 | 3/2003 | Needham et al. |
| 6,206,822 | B1 | 3/2001 | Foley et al. | 6,537,279 B1 | 3/2003 | Michelson |

| | | | | | | |
|---|---|---|---|---|---|---|
| 6,537,320 B1 | 3/2003 | Michelson | | 6,936,050 B2 | 8/2005 | Michelson |
| 6,540,748 B2 | 4/2003 | Lombardo | | 6,936,051 B2 | 8/2005 | Michelson |
| 6,554,832 B2 | 4/2003 | Shluzas | | 6,962,606 B2 | 11/2005 | Michelson |
| 6,554,836 B2 | 4/2003 | Michelson | | 6,964,664 B2 | 11/2005 | Freid et al. |
| 6,558,387 B2 | 5/2003 | Errico et al. | | 6,966,912 B2 | 11/2005 | Michelson |
| 6,558,423 B1 | 5/2003 | Michelson | | 6,969,390 B2 | 11/2005 | Michelson |
| 6,561,194 B2 | 5/2003 | Michelson | | 6,972,019 B2 | 12/2005 | Michelson |
| 6,565,565 B1 | 5/2003 | Yuan et al. | | 6,972,035 B2 | 12/2005 | Michelson |
| 6,565,571 B1 | 5/2003 | Jackowski et al. | | 6,981,974 B2 | 1/2006 | Berger |
| 6,565,574 B2 | 5/2003 | Michelson | | 6,981,975 B2 | 1/2006 | Michelson |
| 6,575,975 B2 | 6/2003 | Brace et al. | | 6,984,235 B2 | 1/2006 | Huebner |
| 6,575,977 B1 | 6/2003 | Michelson | | 6,986,772 B2 | 1/2006 | Michelson |
| 6,576,970 B2 | 6/2003 | Kim | | 6,989,031 B2 | 1/2006 | Michelson |
| 6,579,290 B1 | 6/2003 | Hardcastle et al. | | 7,001,387 B2 | 2/2006 | Farris et al. |
| 6,582,432 B1 | 6/2003 | Michelson | | 7,001,389 B1 | 2/2006 | Navarro et al. |
| 6,585,769 B1 | 7/2003 | Muhanna et al. | | RE39,035 E | 3/2006 | Finn et al. |
| 6,589,244 B1 | 7/2003 | Sevrain et al. | | 7,008,426 B2 | 3/2006 | Paul |
| 6,592,586 B1 | 7/2003 | Michelson | | 7,008,453 B1 | 3/2006 | Michelson |
| 6,599,290 B2 | 7/2003 | Bailey et al. | | 7,011,663 B2 | 3/2006 | Michelson |
| 6,602,256 B1 | 8/2003 | Hayes | | 7,014,638 B2 | 3/2006 | Michelson |
| 6,605,089 B1 | 8/2003 | Michelson | | 7,022,137 B2 | 4/2006 | Michelson |
| 6,609,322 B1 | 8/2003 | Michelson | | 7,033,394 B2 | 4/2006 | Michelson |
| 6,613,053 B1 | 9/2003 | Collins et al. | | 7,041,105 B2 | 5/2006 | Michelson |
| 6,616,666 B1 | 9/2003 | Michelson | | 7,041,135 B2 | 5/2006 | Michelson |
| 6,620,163 B1 | 9/2003 | Michelson | | 7,044,952 B2 | 5/2006 | Michelson |
| 6,626,907 B2 | 9/2003 | Campbell et al. | | 7,048,739 B2 | 5/2006 | Konieczynski et al. |
| 6,645,208 B2 | 11/2003 | Apfelbaum et al. | | 7,052,499 B2 | 5/2006 | Steger et al. |
| 6,652,525 B1 | 11/2003 | Assaker et al. | | 7,060,067 B2 | 6/2006 | Needham et al. |
| 6,652,584 B2 | 11/2003 | Michelson | | 7,074,221 B2 | 7/2006 | Michelson |
| 6,666,890 B2 | 12/2003 | Michelson | | 7,077,844 B2 | 7/2006 | Michelson |
| 6,669,700 B1 | 12/2003 | Farris et al. | | 7,081,117 B2 | 7/2006 | Bono et al. |
| 6,679,833 B2 | 1/2004 | Smith et al. | | 7,104,991 B2 | 9/2006 | Dixon et al. |
| 6,685,706 B2 | 2/2004 | Padget et al. | | 7,115,142 B2 | 10/2006 | Muhanna et al. |
| 6,689,133 B2 | 2/2004 | Morrison et al. | | 7,156,850 B2 | 1/2007 | Kim |
| 6,692,501 B2 | 2/2004 | Michelson | | 7,166,111 B2 | 1/2007 | Kolb |
| 6,692,503 B2 | 2/2004 | Foley et al. | | 7,169,150 B2 | 1/2007 | Shipp et al. |
| 6,695,849 B2 | 2/2004 | Michelson | | 7,175,623 B2 | 2/2007 | Thramann et al. |
| 6,702,817 B2 | 3/2004 | Beger et al. | | 7,175,624 B2 | 2/2007 | Konieczynski et al. |
| 6,709,458 B2 | 3/2004 | Michelson | | 7,204,837 B2 | 4/2007 | Paul |
| 6,712,818 B1 | 3/2004 | Michelson | | 7,220,263 B2 | 5/2007 | Cordaro |
| 6,716,247 B2 | 4/2004 | Michelson | | 7,229,442 B2 | 6/2007 | Schafer |
| 6,730,127 B2 | 5/2004 | Michelson | | 7,273,481 B2 | 9/2007 | Lombardo et al. |
| 6,733,535 B2 | 5/2004 | Michelson | | 7,288,094 B2 | 10/2007 | Lindemann et al. |
| 6,736,817 B2 | 5/2004 | Troxell et al. | | 7,288,095 B2 | 10/2007 | Baynham et al. |
| 6,749,636 B2 | 6/2004 | Michelson | | 7,300,282 B2 | 11/2007 | Sapian |
| 6,752,812 B1 | 6/2004 | Truwit | | 7,306,605 B2 | 12/2007 | Ross |
| 6,752,832 B2 | 6/2004 | Neumann | | 7,468,069 B2 | 12/2008 | Baynham et al. |
| 6,755,829 B1 | 6/2004 | Bono et al. | | 2001/0000532 A1 | 4/2001 | Michelson |
| 6,755,833 B1 | 6/2004 | Paul et al. | | 2001/0005468 A1 | 6/2001 | Troxell |
| 6,758,849 B1 | 7/2004 | Michelson | | 2001/0005786 A1 | 6/2001 | Michelson |
| 6,761,721 B2 | 7/2004 | Burgess et al. | | 2001/0010020 A1 | 7/2001 | Michelson |
| 6,767,367 B1 | 7/2004 | Michelson | | 2001/0037112 A1 | 11/2001 | Brace et al. |
| 6,770,074 B2 | 8/2004 | Michelson | | 2001/0047171 A1 | 11/2001 | Troxell et al. |
| 6,780,186 B2 | 8/2004 | Errico et al. | | 2001/0047172 A1 | 11/2001 | Foley et al. |
| 6,786,110 B1 | 9/2004 | Broderick | | 2001/0047207 A1 | 11/2001 | Michelson |
| 6,793,655 B2 | 9/2004 | Orsak | | 2001/0047208 A1 | 11/2001 | Michelson |
| 6,793,658 B2 | 9/2004 | LeHuec et al. | | 2002/0004661 A1 | 1/2002 | Sevrain et al. |
| 6,793,679 B2 | 9/2004 | Michelson | | 2002/0013624 A1 | 1/2002 | Michelson |
| 6,808,537 B2 | 10/2004 | Michelson | | 2002/0016595 A1 | 2/2002 | Michelson |
| 6,814,756 B1 | 11/2004 | Michelson | | 2002/0022843 A1 | 2/2002 | Michelson |
| 6,827,740 B1 | 12/2004 | Michelson | | 2002/0026194 A1 | 2/2002 | Morrison et al. |
| 6,840,940 B2 | 1/2005 | Ralph et al. | | 2002/0029040 A1 | 3/2002 | Morrison et al. |
| 6,849,093 B2 | 2/2005 | Michelson | | 2002/0045896 A1 | 4/2002 | Michelson |
| 6,858,031 B2 | 2/2005 | Morrison et al. | | 2002/0045898 A1 | 4/2002 | Freid et al. |
| 6,875,213 B2 | 4/2005 | Michelson | | 2002/0045899 A1 | 4/2002 | Errico et al. |
| 6,884,242 B2 | 4/2005 | LeHuec et al. | | 2002/0058939 A1 | 5/2002 | Wagner et al. |
| 6,890,334 B2 | 5/2005 | Brace et al. | | 2002/0065517 A1 | 5/2002 | Paul |
| 6,890,355 B2 | 5/2005 | Michelson | | 2002/0077641 A1 | 6/2002 | Michelson |
| 6,896,680 B2 | 5/2005 | Michelson | | 2002/0091390 A1 | 7/2002 | Michelson |
| 6,916,320 B2 | 7/2005 | Michelson | | 2002/0091392 A1 | 7/2002 | Michelson |
| 6,923,810 B1 | 8/2005 | Michelson | | 2002/0095155 A1 | 7/2002 | Michelson |
| 6,923,830 B2 | 8/2005 | Michelson | | 2002/0099378 A1 | 7/2002 | Michelson |
| 6,926,718 B1 | 8/2005 | Michelson | | 2002/0099386 A1 | 7/2002 | Beger |

| | | | | | | |
|---|---|---|---|---|---|---|
| 2002/0120272 A1 | 8/2002 | Yuan | | 2004/0039387 A1 | 2/2004 | Gause et al. |
| 2002/0120273 A1 | 8/2002 | Needham | | 2004/0059419 A1 | 3/2004 | Michelson |
| 2002/0123753 A1 | 9/2002 | Michelson | | 2004/0059420 A1 | 3/2004 | Michelson |
| 2002/0128655 A1 | 9/2002 | Michelson | | 2004/0064185 A1 | 4/2004 | Michelson |
| 2002/0128659 A1 | 9/2002 | Michelson | | 2004/0068259 A1 | 4/2004 | Michelson |
| 2002/0138144 A1 | 9/2002 | Michelson | | 2004/0073217 A1 | 4/2004 | Michelson |
| 2002/0143401 A1 | 10/2002 | Michelson | | 2004/0078039 A1 | 4/2004 | Michelson |
| 2002/0147450 A1 | 10/2002 | LeHuec et al. | | 2004/0082958 A1 | 4/2004 | Michelson |
| 2002/0151899 A1 | 10/2002 | Bailey et al. | | 2004/0093084 A1 | 5/2004 | Michelson |
| 2002/0161442 A1 | 10/2002 | Michelson | | 2004/0093085 A1 | 5/2004 | Michelson |
| 2002/0161443 A1 | 10/2002 | Michelson | | 2004/0093086 A1 | 5/2004 | Michelson |
| 2002/0169456 A1 | 11/2002 | Tu et al. | | 2004/0097934 A1 | 5/2004 | Farris et al. |
| 2002/0177897 A1 | 11/2002 | Michelson | | 2004/0097940 A1 | 5/2004 | Paul |
| 2002/0183749 A1 | 12/2002 | Burgess et al. | | 2004/0097950 A1 | 5/2004 | Foley et al. |
| 2002/0183754 A1 | 12/2002 | Michelson | | 2004/0102848 A1 | 5/2004 | Michelson |
| 2002/0183755 A1 | 12/2002 | Michelson | | 2004/0117018 A1 | 6/2004 | Michelson |
| 2002/0183756 A1 | 12/2002 | Michelson | | 2004/0122426 A1 | 6/2004 | Michelson |
| 2002/0183757 A1 | 12/2002 | Michelson | | 2004/0127896 A1 | 7/2004 | Lombardo et al. |
| 2002/0188296 A1 | 12/2002 | Michelson | | 2004/0127897 A1 | 7/2004 | Freid et al. |
| 2002/0198532 A1 | 12/2002 | Michelson | | 2004/0127899 A1 | 7/2004 | Konieczynski et al. |
| 2002/0198533 A1 | 12/2002 | Geisler et al. | | 2004/0127900 A1* | 7/2004 | Konieczynski et al. ........ 606/69 |
| 2003/0014054 A1 | 1/2003 | Huebner | | 2004/0133277 A1 | 7/2004 | Michelson |
| 2003/0018335 A1 | 1/2003 | Michelson | | 2004/0138672 A1 | 7/2004 | Michelson |
| 2003/0023307 A1 | 1/2003 | Michelson | | 2004/0138751 A1 | 7/2004 | Michelson |
| 2003/0040749 A1 | 2/2003 | Grabowski et al. | | 2004/0138752 A1 | 7/2004 | Michelson |
| 2003/0040798 A1 | 2/2003 | Michelson | | 2004/0153069 A1 | 8/2004 | Paul |
| 2003/0045880 A1 | 3/2003 | Michelson | | 2004/0153092 A1 | 8/2004 | Beger et al. |
| 2003/0050701 A1 | 3/2003 | Michelson | | 2004/0153878 A1 | 8/2004 | Bromwich et al. |
| 2003/0056795 A1 | 3/2003 | Michelson | | 2004/0158246 A1 | 8/2004 | Assaker et al. |
| 2003/0060828 A1 | 3/2003 | Michelson | | 2004/0158251 A1 | 8/2004 | Morrison et al. |
| 2003/0065394 A1 | 4/2003 | Michelson | | 2004/0162563 A1 | 8/2004 | Michelson |
| 2003/0065396 A1 | 4/2003 | Michelson | | 2004/0172131 A1 | 9/2004 | Michelson |
| 2003/0074001 A1 | 4/2003 | Apfelbaum et al. | | 2004/0176763 A1 | 9/2004 | Foley et al. |
| 2003/0078668 A1 | 4/2003 | Michelson | | 2004/0176765 A1 | 9/2004 | Troxell et al. |
| 2003/0083667 A1 | 5/2003 | Ralph et al. | | 2004/0181226 A1 | 9/2004 | Michelson |
| 2003/0100949 A1 | 5/2003 | Michelson | | 2004/0181229 A1 | 9/2004 | Michelson |
| 2003/0105462 A1 | 6/2003 | Haider | | 2004/0181233 A1 | 9/2004 | Michelson |
| 2003/0120344 A1 | 6/2003 | Michelson | | 2004/0181286 A1 | 9/2004 | Michelson |
| 2003/0125742 A1 | 7/2003 | Yuan et al. | | 2004/0186346 A1 | 9/2004 | Smith et al. |
| 2003/0130662 A1 | 7/2003 | Michelson | | 2004/0186476 A1 | 9/2004 | Michelson |
| 2003/0135213 A1 | 7/2003 | LeHuec et al. | | 2004/0186499 A1 | 9/2004 | Michelson |
| 2003/0135279 A1 | 7/2003 | Michelson | | 2004/0204710 A1 | 10/2004 | Patenl et al. |
| 2003/0139648 A1 | 7/2003 | Foley et al. | | 2004/0204712 A1 | 10/2004 | Kolb et al. |
| 2003/0139816 A1 | 7/2003 | Michelson | | 2004/0204716 A1 | 10/2004 | Fanger et al. |
| 2003/0149434 A1 | 8/2003 | Paul | | 2004/0204717 A1 | 10/2004 | Fanger et al. |
| 2003/0149482 A1 | 8/2003 | Michelson | | 2004/0210232 A1 | 10/2004 | Patel et al. |
| 2003/0149483 A1 | 8/2003 | Michelson | | 2004/0210313 A1 | 10/2004 | Michelson |
| 2003/0149484 A1 | 8/2003 | Michelson | | 2004/0210314 A1 | 10/2004 | Michelson |
| 2003/0149486 A1 | 8/2003 | Huebner | | 2004/0215203 A1 | 10/2004 | Michelson |
| 2003/0153916 A1 | 8/2003 | Michelson | | 2004/0220571 A1 | 11/2004 | Assaker et al. |
| 2003/0158553 A1 | 8/2003 | Michelson | | 2004/0220572 A1 | 11/2004 | Michelson |
| 2003/0171754 A1 | 9/2003 | Del Medico | | 2004/0230308 A1 | 11/2004 | Michelson |
| 2003/0181912 A1 | 9/2003 | Michelson | | 2004/0236331 A1 | 11/2004 | Michelson |
| 2003/0187448 A1 | 10/2003 | Michelson | | 2004/0236334 A1 | 11/2004 | Michelson |
| 2003/0191471 A1 | 10/2003 | Michelson | | 2004/0236335 A1 | 11/2004 | Michelson |
| 2003/0191472 A1 | 10/2003 | Michelson | | 2004/0249388 A1 | 12/2004 | Michelson |
| 2003/0195517 A1 | 10/2003 | Michelson | | 2004/0260306 A1 | 12/2004 | Fallin et al. |
| 2003/0195624 A1 | 10/2003 | Muhanna et al. | | 2004/0267274 A1 | 12/2004 | Patel et al. |
| 2003/0199874 A1 | 10/2003 | Michelson | | 2005/0010225 A1 | 1/2005 | Del Medico |
| 2003/0199876 A1 | 10/2003 | Brace et al. | | 2005/0010227 A1 | 1/2005 | Paul |
| 2003/0199983 A1 | 10/2003 | Michelson | | 2005/0010294 A1 | 1/2005 | Michelson |
| 2003/0203745 A1 | 10/2003 | Chiang et al. | | 2005/0010295 A1 | 1/2005 | Michelson |
| 2003/0208204 A1 | 11/2003 | Bailey et al. | | 2005/0015092 A1 | 1/2005 | Rathbun et al. |
| 2003/0208270 A9 | 11/2003 | Michelson | | 2005/0015093 A1 | 1/2005 | Suh et al. |
| 2003/0208275 A1 | 11/2003 | Michelson | | 2005/0015149 A1 | 1/2005 | Michelson |
| 2003/0216740 A1 | 11/2003 | Michelson | | 2005/0021041 A1 | 1/2005 | Michelson |
| 2004/0024400 A1 | 2/2004 | Michelson | | 2005/0021150 A1 | 1/2005 | Michelson |
| 2004/0024464 A1 | 2/2004 | Errico et al. | | 2005/0027293 A1 | 2/2005 | LeHuec et al. |
| 2004/0030338 A1 | 2/2004 | Paul | | 2005/0027297 A1 | 2/2005 | Michelson |
| 2004/0034352 A1 | 2/2004 | Needham et al. | | 2005/0027298 A1 | 2/2005 | Michelson |
| 2004/0034353 A1 | 2/2004 | Michelson | | 2005/0033296 A1 | 2/2005 | Bono et al. |
| 2004/0034354 A1 | 2/2004 | Paul | | 2005/0033298 A1 | 2/2005 | Hawkes et al. |
| 2004/0034358 A1 | 2/2004 | Michelson | | 2005/0033433 A1 | 2/2005 | Michelson |

| | | | |
|---|---|---|---|
| 2005/0038436 A1 | 2/2005 | Michelson | |
| 2005/0038444 A1 | 2/2005 | Binder et al. | |
| 2005/0038512 A1 | 2/2005 | Michelson | |
| 2005/0038513 A1 | 2/2005 | Michelson | |
| 2005/0039568 A1 | 2/2005 | Broderick | |
| 2005/0043741 A1 | 2/2005 | Michelson | |
| 2005/0049593 A1 | 3/2005 | Duong et al. | |
| 2005/0059971 A1 | 3/2005 | Michelson | |
| 2005/0060037 A1 | 3/2005 | Michelson | |
| 2005/0065518 A1 | 3/2005 | Michelson | |
| 2005/0065519 A1 | 3/2005 | Michelson | |
| 2005/0065608 A1 | 3/2005 | Michelson | |
| 2005/0085816 A1 | 4/2005 | Michelson | |
| 2005/0137606 A1 | 6/2005 | Binder et al. | |
| 2005/0165399 A1 | 7/2005 | Michelson | |
| 2005/0165489 A1 | 7/2005 | Michelson | |
| 2005/0171606 A1 | 8/2005 | Michelson | |
| 2005/0171607 A1 | 8/2005 | Michelson | |
| 2005/0177154 A1 | 8/2005 | Moumene et al. | |
| 2005/0187552 A1 | 8/2005 | Michelson | |
| 2005/0187554 A1 | 8/2005 | Michelson | |
| 2005/0187628 A1 | 8/2005 | Michelson | |
| 2005/0187629 A1 | 8/2005 | Michelson | |
| 2005/0192576 A1 | 9/2005 | Michelson | |
| 2005/0216009 A1 | 9/2005 | Michelson | |
| 2005/0216010 A1 | 9/2005 | Michelson | |
| 2005/0216011 A1 | 9/2005 | Paul | |
| 2005/0216083 A1 | 9/2005 | Michelson | |
| 2005/0216085 A1 | 9/2005 | Michelson | |
| 2005/0216089 A1 | 9/2005 | Michelson | |
| 2005/0228386 A1* | 10/2005 | Ziolo et al. | 606/69 |
| 2005/0228398 A1 | 10/2005 | Rathbun et al. | |
| 2005/0234452 A1 | 10/2005 | Malandain | |
| 2005/0234455 A1* | 10/2005 | Binder et al. | 606/69 |
| 2005/0234456 A1 | 10/2005 | Malandain | |
| 2005/0251137 A1* | 11/2005 | Ball | 606/61 |
| 2005/0261690 A1 | 11/2005 | Binder et al. | |
| 2005/0267578 A1 | 12/2005 | Michelson | |
| 2005/0270489 A1 | 12/2005 | Michelson | |
| 2005/0273105 A1 | 12/2005 | Konieczynski et al. | |
| 2005/0288671 A1 | 12/2005 | Yuan et al. | |
| 2006/0036247 A1 | 2/2006 | Michelson | |
| 2006/0058793 A1 | 3/2006 | Michelson | |
| 2006/0122604 A1 | 6/2006 | Gorhan et al. | |

FOREIGN PATENT DOCUMENTS

| | | |
|---|---|---|
| DE | 4409833 | 10/1995 |
| DE | 4414781 | 11/1995 |
| DE | 19944120 | 3/2001 |
| DE | 10005385 | 8/2001 |
| DE | 10065232 | 11/2002 |
| DE | 202004015912 | 1/2005 |
| EP | 0270704 | 6/1988 |
| EP | 0348272 | 12/1989 |
| EP | 0506420 | 9/1992 |
| EP | 0554915 | 8/1993 |
| EP | 0865259 | 9/1998 |
| EP | 0997107 | 5/2000 |
| EP | 1090595 | 4/2001 |
| EP | 1106144 | 6/2001 |
| FR | 22444446 | 4/1975 |
| FR | 2435243 | 4/1980 |
| FR | 2642642 | 8/1990 |
| FR | 2740321 | 4/1997 |
| WO | WO88/03781 | 6/1988 |
| WO | WO90/02526 | 3/1990 |
| WO | WO94/17744 | 8/1994 |
| WO | WO94/26193 | 11/1994 |
| WO | WO95/11632 | 5/1995 |
| WO | WO95/31941 | 11/1995 |
| WO | WO95/35067 | 12/1995 |
| WO | WO96/08206 | 3/1996 |
| WO | WO96/39975 | 12/1996 |

OTHER PUBLICATIONS

Ronald I. Apfelabuma, et al., Clinical Experience with a New Load-Sharing Anterior Cervical Plate, Elsevier Science, Feb. 7, 2003.

Stephen I. Esses, et al., Cervical Plates: Comparison of Physical Characteristics and in Vitro Pushout Strength, The Spine Journal, Mar. 2003, pp. 118-124.

George, J. Haidukewych, Innovations in Locking Plate Technology, Am Acad Orthop Surg., Jul. 2004, pp. 205-212, vol. 12, No. 4.

Ibhrahim Omeis, et al., History of Instrumentation for Stabilization of the subaxial Cervical Spine, Neurosurgical Focus, Jan. 2004, vol. 16, No. 1.

Eriko O. Martz, et al., Materials and Design of Spinal Implants—A review, Journal of Biomedical Materials Research, Dec. 6, 1998.

Regis W. Haid, et al., The Cervical Spine Study Group Anterior Cervical Plate Nomenclature, Neurosurgical Focus, Jan. 15, 2002, vol. 12.

Apfelbaum, et al., Surgical Technique, ABC Advanced Biomedical Concept, AESCULAP®, pp. 1-18.

Wolfhard Caspar, Anterior Cervical Fusion and Interbody Stabilization with the Trapezial Osteosynthetic Plate Technique, AESCULAP® Scientific Information, Oct. 1984, 5$^{th}$ revised and extended issue-1$^{st}$ issued Dec. '82, 6 pages.

Ordering Information for Implants and Instruments, AcroPlate™ Anterior Cervical System, © 1994 AcroMed Corporation, 6 pages.

Haid, et al., The Cervical Spine Study Group anterior cervical plate nomenclature, Neurosurg. Focus, Jan. 2002, vol. 12, 6 pages.

ABC-System, B. Braun Melsungen AG, retrieved from the Internet on Jun. 3, 2004 at URL: http://www.bbraun.com/index.cfm, 1 page.

Caspar Evolution-System, B. Braun Melsungen AG, retrieved from the Internet on Jun. 3, 2004 at URL: http://www.bbraun.com/index.cfm, 1 page.

Deltaloc™ Anterior Cervical Plate System, Alphatec Manufacturing Inc., retrieved from the Internet on May 28, 2004 at URL: http://www.alphatecmfg/products deltaloc.html, 1 page.

Reveal™ Anterior Cervical Plate System, Alphatec Manufacturing Inc., retrieved from the Internet on May 28, 2004 at URL: http://www.alphatecmfg/products deltalocreveal.html, 1 page.

Window System, A-Spine Holding Group Corp., retrieved from the Internet on Jun. 9, 2004 at URL: http://www.aspine.net/products/windows.html, 2 pages.

Blackstone Classic Anterior Cervical Plate, Blackstone Medical Inc., retrieved from the Internet on Jun. 9, 2004 at URL: http://www.blackstonemedical.com/products/acp.php, 2 pages.

Peak™ Polyaxial Anterior Cervical Plate, DePuySpine Inc., retrieved from the Internet on Jun. 9, 2004 at URL: http://depuyspine.com/products/cervical/peak polyaxial.asp, 2 pages.

The C-TEK® Anterior Cervical Plate System, Interpore Cross International, Inc., retrieved from the Internet on Jun. 9, 2004 at URL: http://www.interpore.com/product ctek.html., 1 page.

Altantis® Anterior Cervical Plate System, Spinal Technologies, Medtronic Sofamor Danek, retrieved from the Internet on Jun. 2, 2004 at URL: http://www.sofamordanek.com/patient-spinal-atlantis.html, 3 pages.

Zephir™ Anterior Cervical Plate System, Spinal Technologies, Medtronic Sofamor Danek, retrieved from the Internet on Jun. 2, 2004 at URL: http://www.sofamordanek.com/patient-spinal-zephir.html, 2 pages.

Seculplate Anterior Cervical Plate, Scientx USA, retrieved from the Internet on Jun. 3, 2004 at URL: http://www.scientxusa.com/index., 1 page.

SC-Acufix™, Spinal Concepts, retrieved from the Internet on Jun. 3, 2004 at URL: http://www.spinalconcepts.com/products/sc_acufix.html, 1 page.

Reflex: Anterior Cerival Plate System, Stryker, retrieved from the Internet on Jun. 9, 2004 at URL: http://www.stryker.com/spine/products cervical reflex.html., 2 pages.

Tether: Anterior Cervical Plate System, Stryker, retrieved from the Internet on Jun. 9, 2004 at URL: http://www.stryker.com/spine/products cervical tether.html., 1 page.

CSLP Cervical Locking Plate, Synthes Products, retrieved form the Internet on Jun. 9, 2004 at URL: http://www.synthes-stratec.com/html/CSLP_Cervical_Lockin.4326.0.html, 1 page.

SCP™-Semi-Constrained Cervical Plate, Vertebron™, retrieved from the Internet on Jun. 3, 2004 at URL: http://www.vertebron.com/fusion.htm, 2 pages.

Trinica™ Anterior Cervical Plate System, Zimmer spine, retrieved from the Internet on Jun. 1, 2004 at URL: http://www.zimmerspine.com/spine.products/cervical/trinica/index, 3 pages.

* cited by examiner

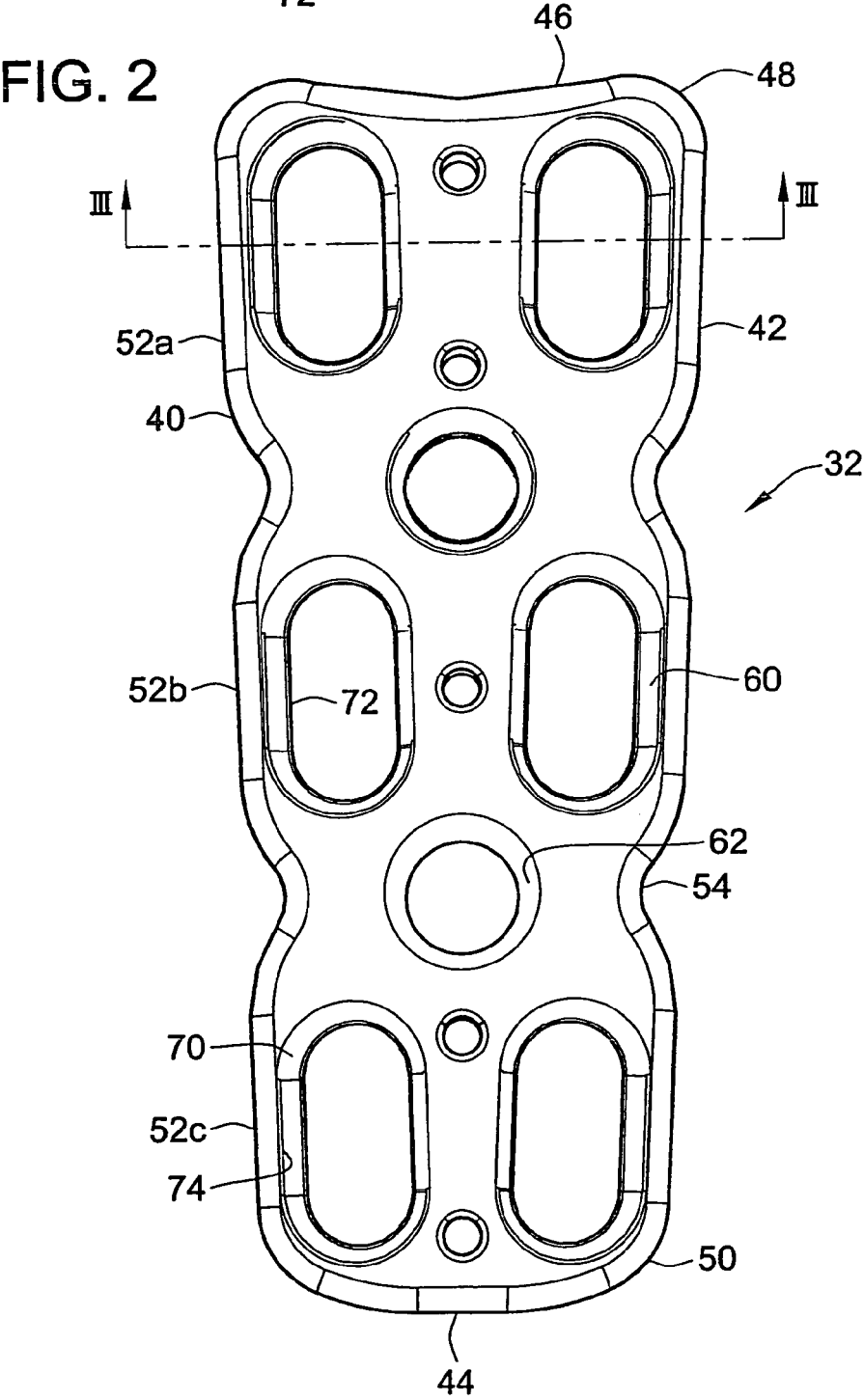

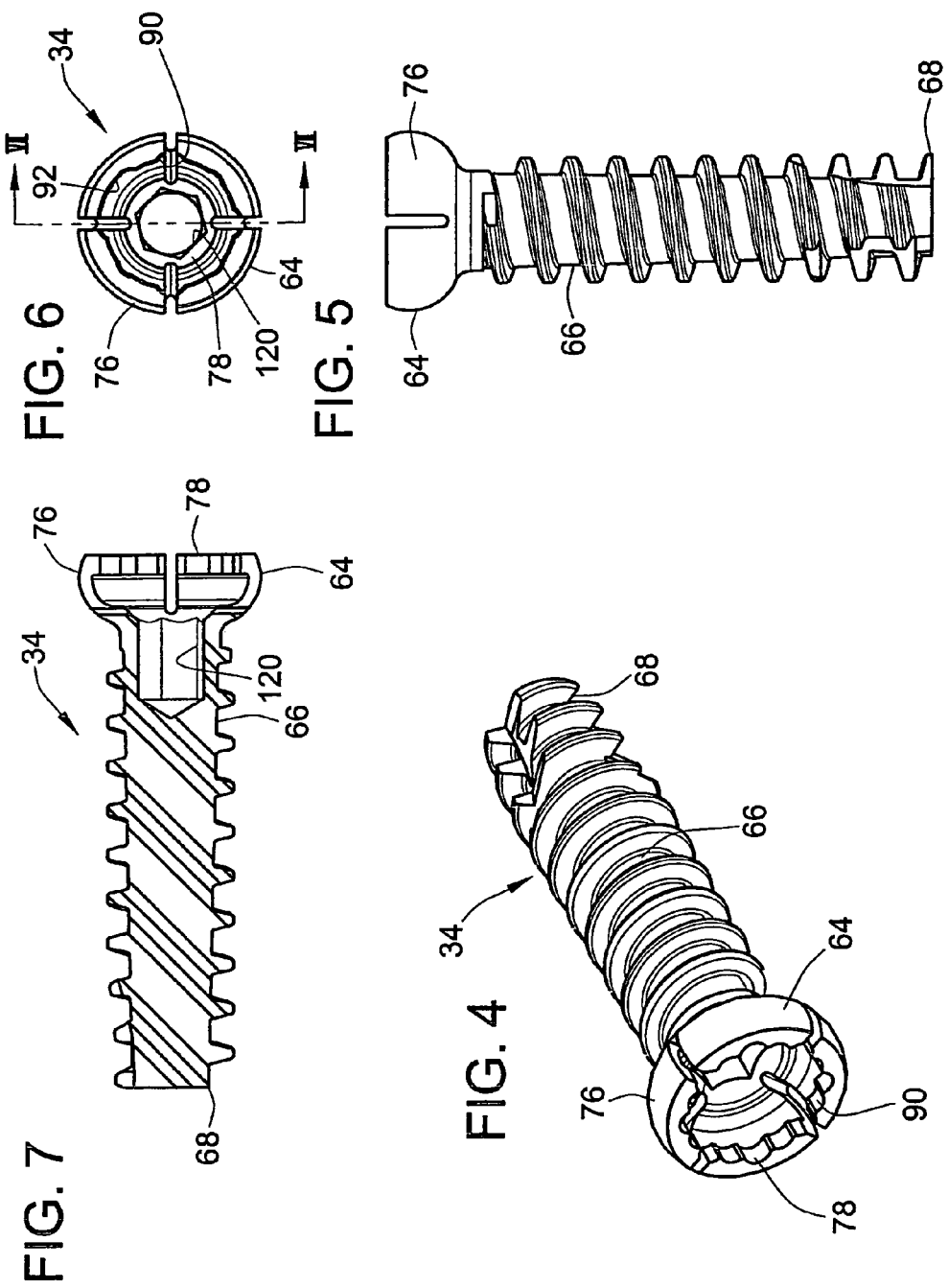

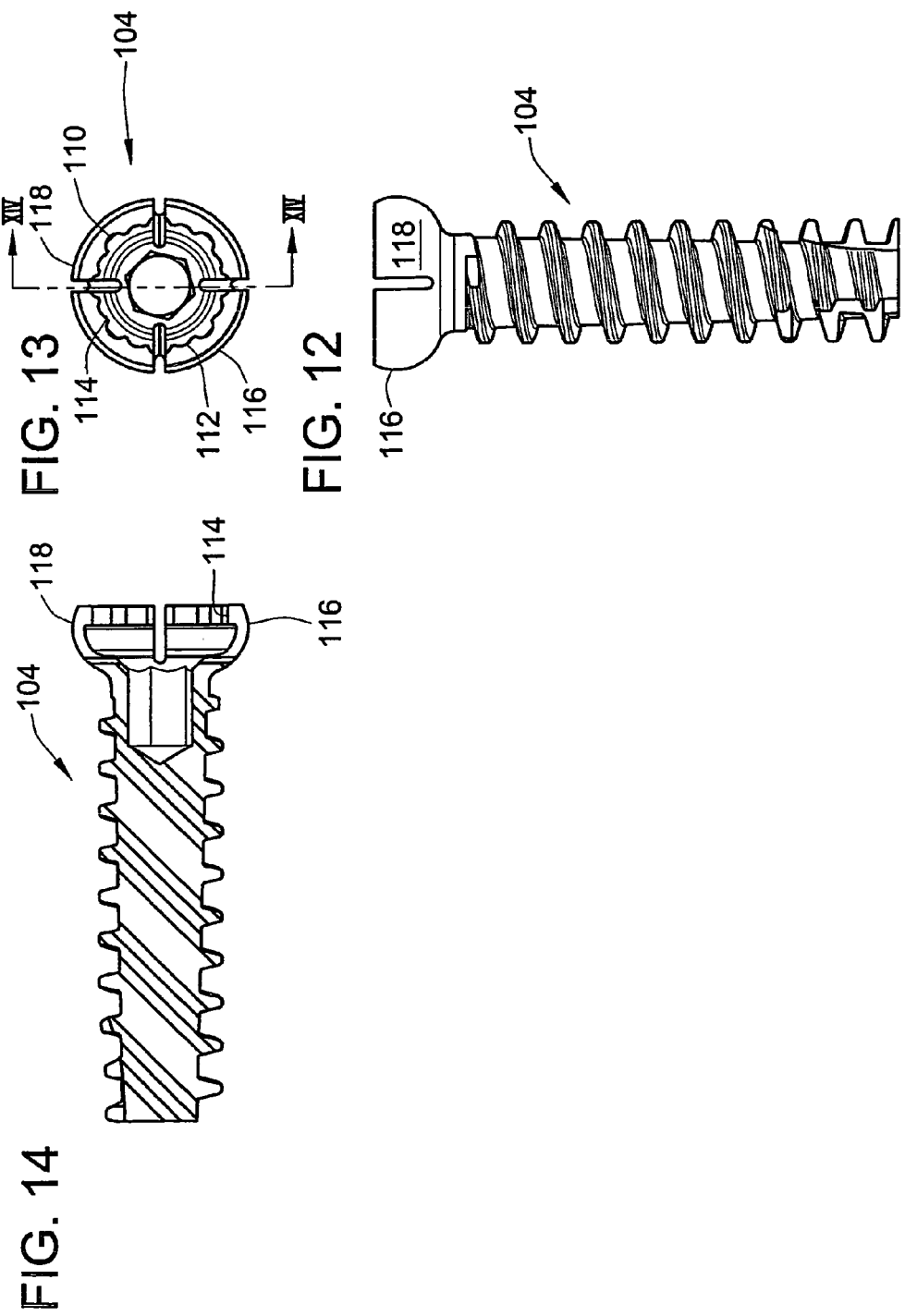

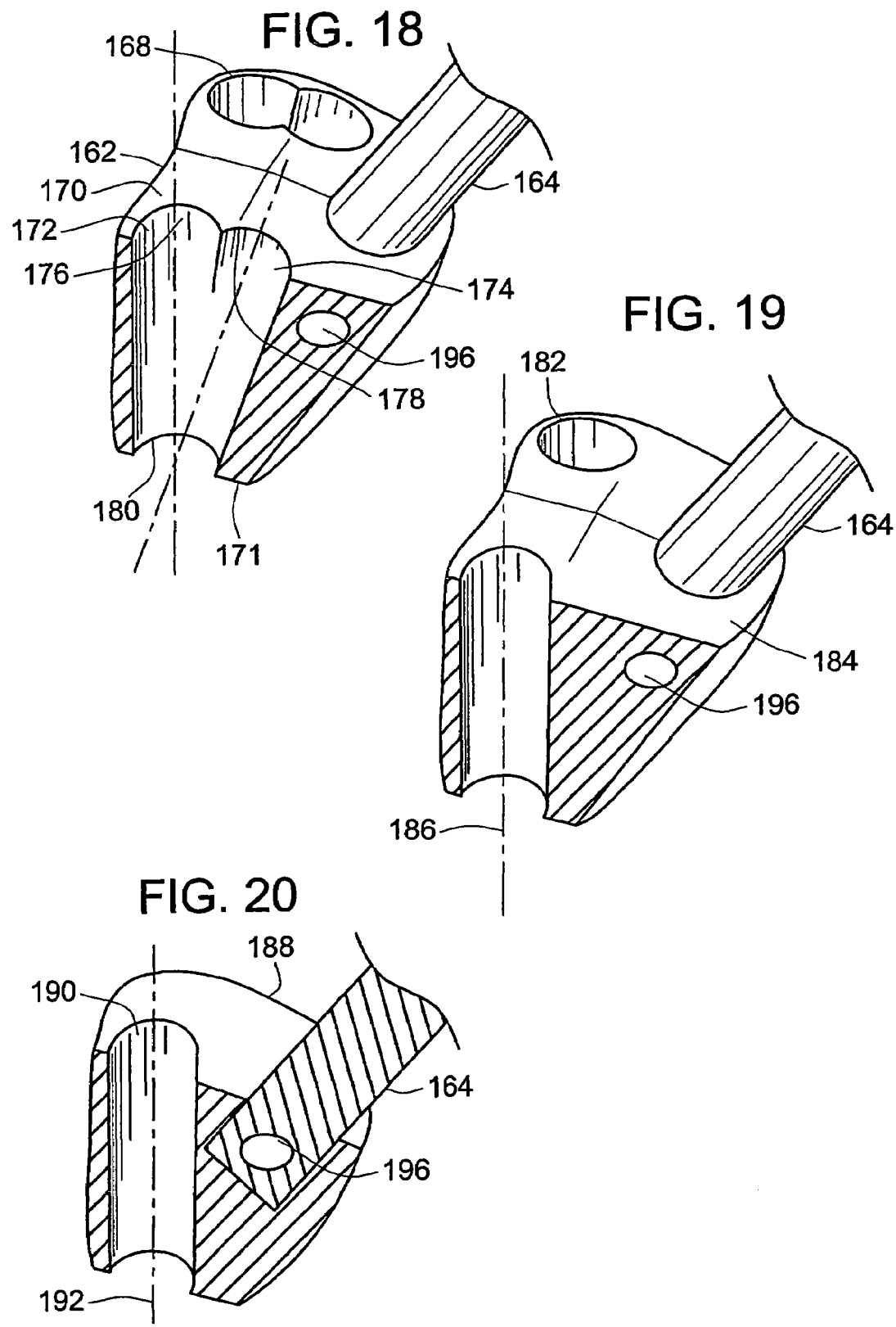

CERVICAL PLATE SYSTEM

RELATED APPLICATIONS

This application claims the benefit of U.S. Provisional Patent Application No. 60/637,690, filed Dec. 21, 2004, the disclosure of which is herein incorporated by reference in its entirety.

FIELD OF THE INVENTION

This invention pertains to implantable orthopaedic devices, and more particularly to a cervical plate and screw arrangement, and a tool and method for implanting the same.

BACKGROUND OF THE INVENTION

Bone fixation devices are useful for promoting proper healing of injured or damaged vertebral bone segments caused by trauma, tumor growth, or degenerative disc disease. The external fixation devices are commonly utilized to immobilize the injured bone segments to ensure the proper growth of new osseous tissue between the damaged segments. These types of external bone fixation devices often include internal bracing and instrumentation to stabilize the spinal column to facilitate the efficient healing of the damaged area without deformity or instability, while minimizing any immobilization and post-operative care of the patient.

One such device is an osteosynthesis or bone fixation plate, which can be used to immobilize adjacent vertebrae. Typically, the fixation plate is a rigid metal or polymeric plate positioned to span bones or bone segments that require immobilization with respect to one another. The plate is fastened to the respective bones, usually with bone screws driven into the vertebral bodies. In this way, the plate is secured to the spine, fixing the respective vertebrae in a desired position. Bone plates can be useful in providing the mechanical support necessary to keep vertebral bodies in proper position and bridge a weakened or diseased area such as when a disc, vertebral body or fragment has been removed. Exemplary systems are disclosed in U.S. Published Application 2003/0187443 A1 to Lauryssen et al., U.S. Pat. No. 6,159,213 to Rogozinski, U.S. Pat. No. 6,152,927, U.S. Pat. No. 6,017,345 to Richelsoph, U.S. Pat. No. 5,676,666 to Oxland et al., U.S. Pat. No. 5,616,144 to Yapp et al., U.S. Pat. No. 5,549,612 to Yapp et al., U.S. Pat. No. 5,261,910 to Warden et al., and U.S. Pat. No. 4,696,290 to Steffee.

Accordingly, there exists a need for a plate system and method of placement of the same that provides the advantages of the currently available arrangements, while minimizing or eliminating the disadvantages of the same. There remains a need for an anterior bone plate system that minimizes any soft tissue and osseous tissue damage that would occur with its implementation, that is easy to use, and that provides the surgeon with flexibility in placement of the same. The system must be able to provide effective fixation and immobilization of vertebral bodies, while also providing for the subsidence necessary for proper fusion and prevent axial extension of the plate. The invention provides such an arrangement. The advantages of the invention, as well as additional inventive features, will be apparent from the description of the invention provided herein.

BRIEF DESCRIPTION OF THE DRAWINGS

FIG. 2 is a plan view of the bone plate of FIG. 1.

FIG. 3 is a cross-sectional view of the bone plate of FIGS. 1 and 2 taken along line III-III in FIG. 2.

FIG. 4 is a perspective view of a bone screw constructed in accordance with teachings of the invention.

FIG. 5 is a side elevational view of the bone screw of FIG. 4.

FIG. 6 is a top plan view of the bone screw of FIGS. 4 and 5.

FIG. 7 is a cross-sectional view of the bone screw of FIGS. 4-6 taken along line VII-VII in FIG. 6.

FIG. 12 is a side elevational view of an alternate embodiment of a bone screw constructed in accordance with teachings of the invention.

FIG. 13 is a top plan view of the bone screw of FIG. 12.

FIG. 14 is a cross-sectional view of the bone screw of FIGS. 12-13 taken along line XIV-XIV in FIG. 13.

FIG. 18 is an enlarged, fragmentary, cross-sectional view of the guide block of FIG. 17.

FIG. 19 is an enlarged, fragmentary, cross-sectional view of an alternate embodiment of a guide block of a tool.

FIG. 20 is an enlarged, fragmentary, cross-sectional view of yet another alternate embodiment of a guide block of a tool.

DETAILED DESCRIPTION OF THE INVENTION

Figure 1:
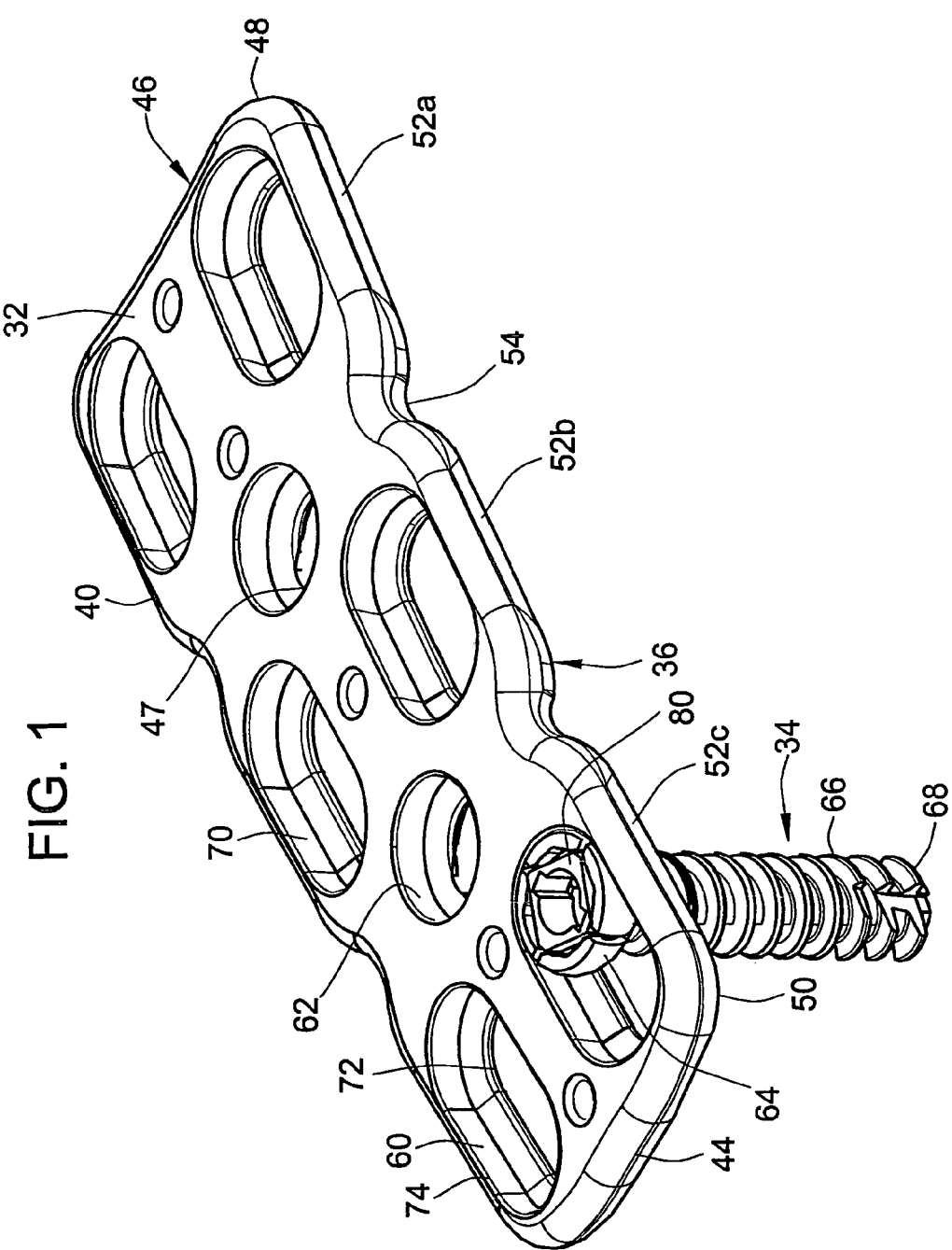
FIG. 1 is a perspective view of a bone plate and bone screw assembly constructed in accordance with teachings of the invention. A plurality of such bone screws would be provided in the assembly.

Turning now to the drawings, there is shown in FIGS. 1-3 an exemplary embodiment of an assembly 30 of a bone plate 32 and one of a plurality of bone screws 34 constructed in accordance with teachings of the invention. The bone plate 32 is an elongated structure having a lower surface 36 adapted to be placed against a plurality of vertebrae (not illustrated), and an upper surface 38 opposite the lower surface 36. Disposed between the lower and upper surfaces 36, 38 are side surfaces 40, 42 and end surfaces 44, 46. In order to minimize undue wear and any irritation to soft tissue surrounding the plate 32 when in position on the skeletal system, the side surfaces 40, 42, 44, 46 are generally rounded, as may be seen in FIGS. 1 and 3. To anchor the bone plate 32 to the bony surface, the lower surface 36 of the plate 32 is preferably provided with cleats or ridges (see, e.g., 47) of any appropriate design.

As may best be seen in FIG. 2, the bone plate 32 has a plan view profile that generally narrows from one longitudinal end 48 to the other 50. To further conform to the vertebral contours, the bone plate lower surface 36 is generally concave in both the longitudinal and lateral directions (see FIGS. 1 and 3). The bone plate 32 may additionally be divided into a plurality of vertebral nodes 52a-c adapted to be coupled to adjacent vertebrae. In the illustrated embodiment, three such nodes 52a-c are provided for immobilizing three bone segments. It will be appreciated, however, that the plate 32 may alternately include two such nodes, or four or more such nodes for immobilizing two or four or more bone segments, respectively. Preferably, recesses 54 are provided between adjacent nodes 52a-c. Such recesses 54 reduce the cross-sectional area of the plate 32 between the respective nodes 52a-c to facilitate bending of the plate 32 as may be desirable to further contour the plate 32 to spinal anatomy.

In order to couple the plate 32 to the vertebrae, the bone plate 32 is provided with a plurality of apertures 60, 62 therethrough for receipt of a plurality of bone screws 34. Preferably, the apertures 60 extending through the respective nodes 52a-c are elongate channels 60 such that a bone screw 34 disposed therein may be positioned at the desired location within the channels 60. In the preferred application of the bone plate 32 to a spinal column, the respective nodes 52a-c are positioned along adjacent vertebrae, and bone screws 34 disposed within the channels 60 are screwed into the vertebrae. In accordance with the invention, channels 60 and apertures 62 through the plate 32 each include a concave edge wall 70. That is, the lower surface opening 72 along the lower surface 36 of the plate 32 and an upper surface opening 74 along the upper surface 38 of the plate 32 are each smaller than the opening within the concave edge wall 70. Preferably, the upper surface opening 74 is larger than the lower surface opening 72.

As shown in more detail in FIGS. 4-7, the exemplary bone screws 34 include an enlarged head 64 from which a threaded shank 66 extends. The distal end 68 of the shank 66 is preferably self-tapping. To permit assembly of the screw 34 into an aperture 60, 62, the outside diameter of the threaded shank 66 is smaller than the minor diameter of the lower surface opening 72 through the plate 32. Preferably, the diameter of the shank is sufficiently smaller than the lower surface opening 72 to allow some pivoting motion of the screw 34 during placement.

According to another aspect of the invention, the enlarged head 64 of the screw 34 is of a generally spherical shape and includes a plurality of spaced, arcuate petal portions 76 disposed around a central opening 78 in the head 64. It will be appreciated by those of skill in the art that the petal-portions 76 may flex radially inward to reduce the outer diameter of the enlarged head 64 of the screw 34. The outer diameter of the enlarged head 64 is preferably larger than the minor diameter of the upper surface opening 74 such that the petal portions 76 of the enlarged head 64 must flex radially inward to allow the enlarged head 64 to be positioned within the concave edge wall 70 of an aperture 60 or channel 62 as the screw 34 is advanced through the aperture 60 or channel 62. Once the petal portions 76 of the head 64 advance past the upper surface opening 74, the petal portions 76 expand again to their free, relaxed state, preferably in slight interference with the inside concave edge wall 70.

Figure 8:
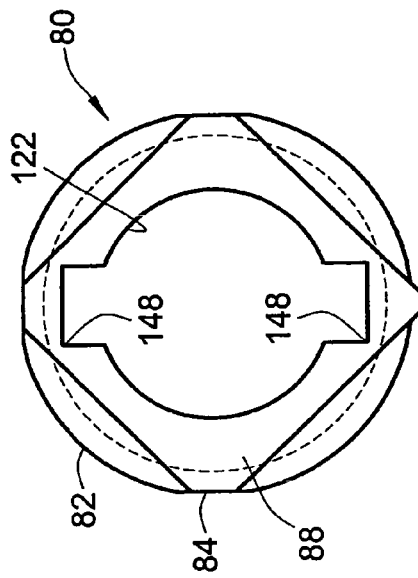
FIG. 8 is a plan view of a locking disc constructed in accordance with teachings of the invention.
Figure 10:
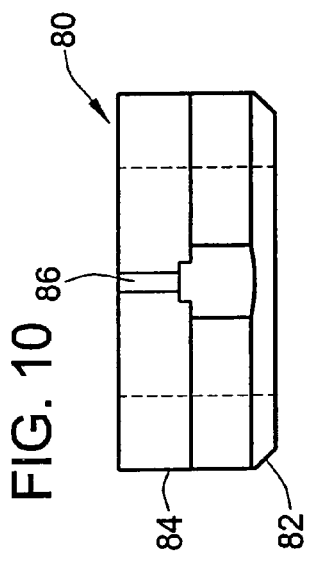
FIG. 10 is a side view of the locking disc of FIGS. 8 and 9 showing the extended protrusion.
Figure 9:
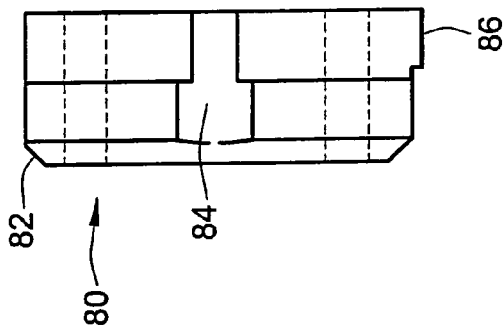
FIG. 9 is a side view of the locking disc of FIG. 8.

In order to maintain the head 64 of the bone screw 34 in the desired position captured within an aperture 60 or channel 62 once the screw shank 66 has been screwed into position within the bone, a locking disc 80 is provided. As shown in FIG. 1, the locking disc 80 is rotatably disposed within the central opening 78 within the head 64. As shown in greater detail in FIGS. 8-10, the locking disc 80 comprises a base portion 82 and extending engaging surfaces (protrusions) 84, 86. In the illustrated embodiment of FIGS. 8-10, the base portion 82 is a circular disc shape, and the engaging surfaces 84, 86 include the corners of a rectangular portion 88 disposed on the circular base portion 82.

As shown in FIG. 1, the locking disc 80 is fully received (nested) within the opening 78 within the head 64 of the screw 34, such that its proximal face does not protrude beyond the proximal end of the screw head 64 (thus minimizing the risk of tissue damage and patient discomfort). The inside surface of the opening 78 includes mating structure 90, such that when the locking disc 80 is in a first rotational position, the petal portions 76 are free to flex inward slightly. The screw may rotate or slide within the aperture 62 or channel 60. Conversely, when the locking disc 80 is in a second rotational position relative to the head 64, the petal portions 76 may not flex inwardly. Rather, they are engaged lightly against the inside, concave wall 70 of the channel 60 or aperture 62 and prevent the screw 34 from escaping the upper surface opening 74 of the channel or aperture in the plate 32. In other words, when high points of the extending protrusions 84, 86 and the mating structure 90 along the inside surface of the central opening 78 engage, the petal portions 76 are prevented from flexing radially inward.

Figure 11:
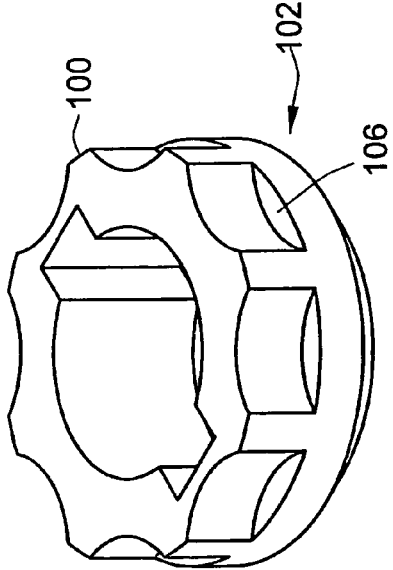
FIG. 11 is a perspective view of an alternate embodiment of a locking disc constructed in accordance with teachings of the invention.

It will be appreciated that various structures of engaging and mating structure may be provided in accordance with teachings of the invention. In the embodiment of FIG. 11, the engaging structure 100 of the locking disc 102 includes an octagonal star shape 106 (having eight protrusions), while the screw 104 includes sixteen recesses 110, 112 in the inner surface of the central opening 114 of the screw head 116. It will be noted that every other of the recesses 110 is substantially deeper than the alternating recesses 112 (that is, each deep recess 110 has a pair of shallower "neighbor" recesses 112). In this way, when the engaging structures 100 of the star shape 106 are disposed in the deep recesses 110 the petal portions 118 of the head 116 will have inward flex, in contrast to when the engaging structures 100 of the star shape 106 are disposed in shallow recesses 112.

Figure 15:
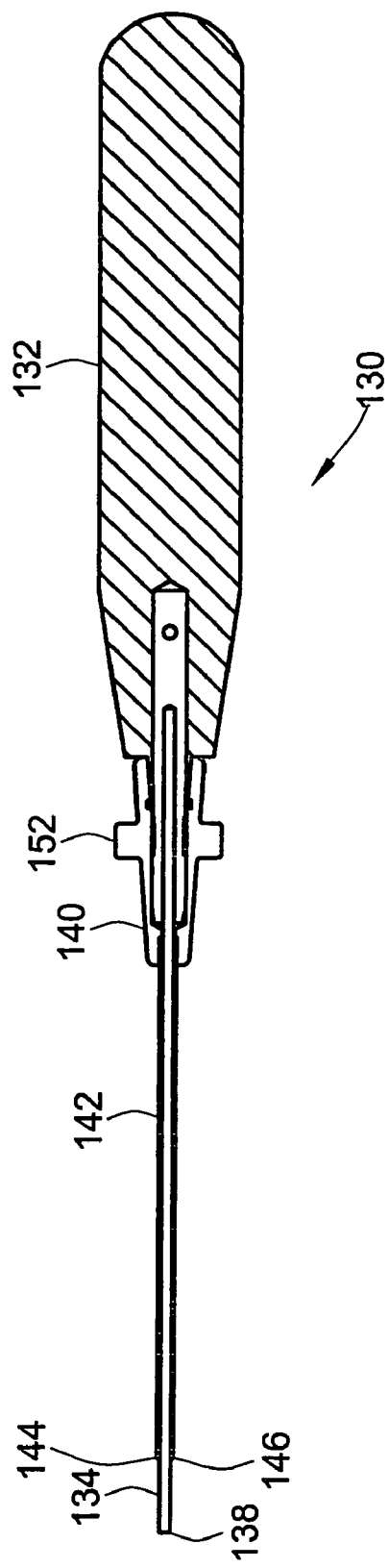
FIG. 15 is a cross-sectional view of an assembly tool constructed in accordance with teachings of the invention.
Figure 16:
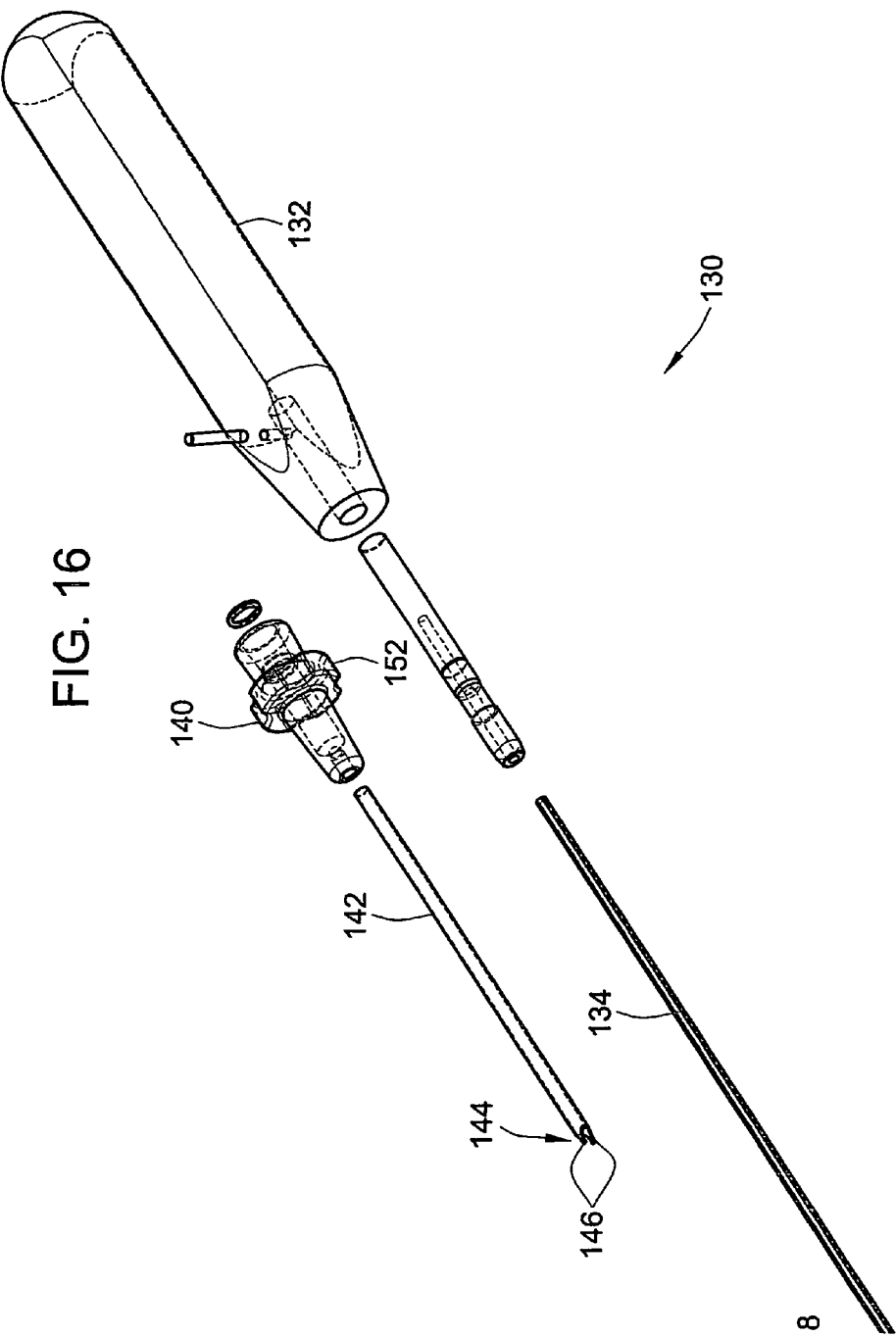
FIG. 16 is an exploded view of the tool of FIG. 15.

Returning to FIGS. 6-7, in order to assemble the screw 34 into the bone, the screw 34 is provided with a bore 120 having an internal defined shape. In the embodiment illustrated, the bore 120 includes a hexagonal shape. It will be appreciated, however, that the bore 120 may be alternately shaped so long as shape is adequate to provide sufficient traction to permit rotation of the screw 34 into the bone. To facilitate access to the bore 120 of the screw 34, the locking disc 80 is provided with an internal bore 122 that is larger than and surrounds the bore 120 of the screw 34 (see FIG. 8). In this way, even when the locking disc 80 is disposed within the head 64 of the screw 34, a tool 130 such as the one illustrated in FIGS. 15 and 16 may be utilized to assemble the screw 34 into the bone.

The tool 130 includes a handle portion 132 from which a screwdriver shaft 134 extends. The distal end 138 of the shaft 136 has a structure that mates with the internal bore 120 of the screw 34 to permit selective rotation thereof. In order to permit selective rotation of the locking disc 80, the tool 130 additionally includes an axially slideable sleeve 140. The sleeve 140 includes a tubular shaft 142 having a distal end 144 with dedicated structure 146 that mates with structure 148 along the internal bore 122 of the locking disc 80. In one embodiment, the internal bore 122 of the locking disc 80 includes recesses 148 along either side of the bore 122 that open onto, and are accessible at, the proximal face of the disc. The distal end 144 of the shaft includes opposing fingers 146 disposed to mate with the recesses 148. To facilitate rotation of the sleeve 140 relative to the shaft 134, the sleeve 140 includes a flange 152.

In use, the surgeon may insert the distal end 138 of the shaft 134 through the internal bore 122 of the locking disc 80 into the internal bore 120 of the screw 34, and rotate the handle portion 132 of the tool 130 to screw the bone screw 34 into the bone. Once properly positioned, the surgeon may axially slide the sleeve 140 to position the opposing fingers 146 within the corresponding recesses 148 of the locking disc 80. Maintaining the position of the bone screw 34 by holding the handle portion 132 stationary, the surgeon may then rotate the flange 152 to rotate the sleeve 140, and, accordingly, the locking disc 80 relative to the stationary screw 34. The surgeon may then remove the tool 130 and attached sleeve 140 from the screw 34 and proceed to the next screw until the plate arrangement 30 is properly placed and secured to the bone.

Figure 17:
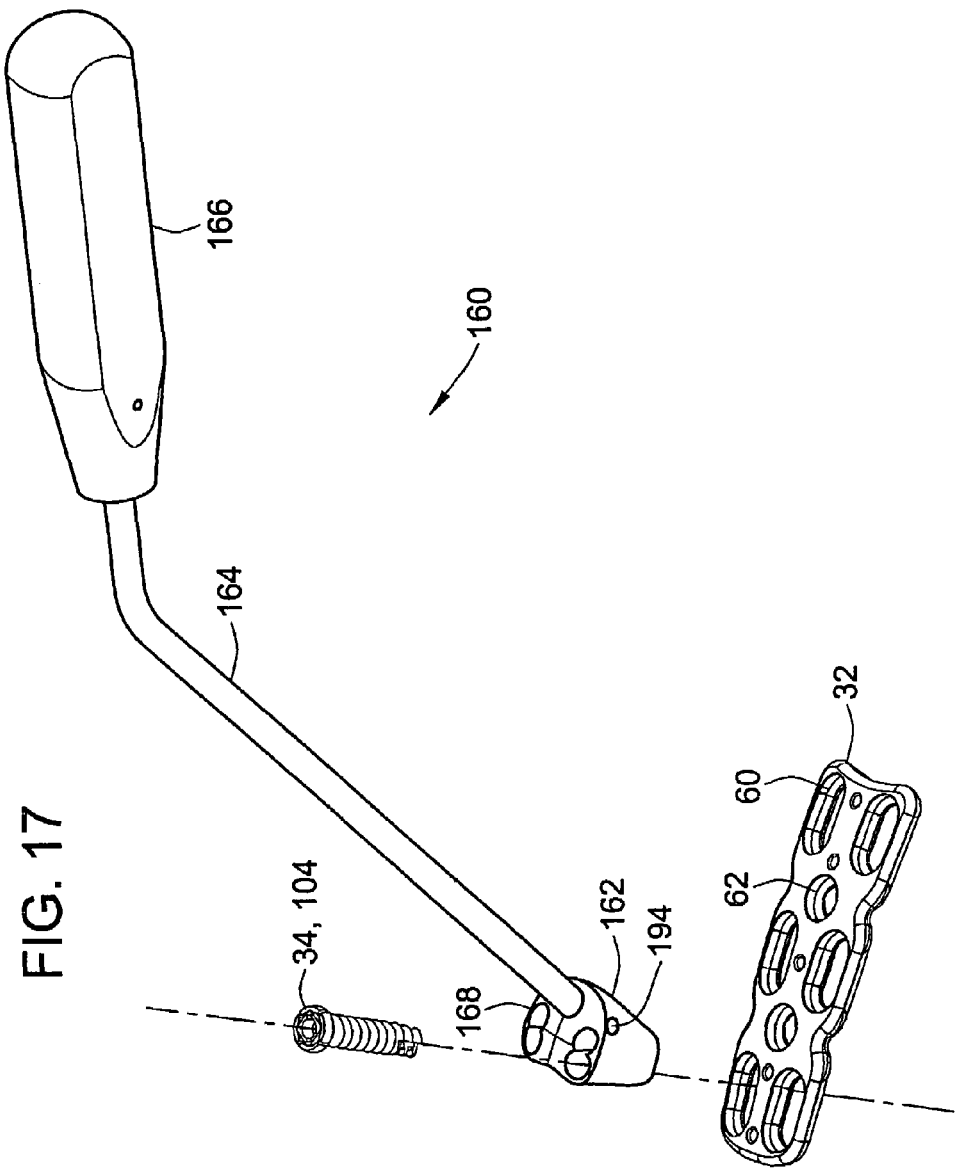
FIG. 17 is a perspective view of a tool including a guide block for insertion of a screw, along with a screw and bone plate.

Those of skill in the art will appreciate that the bone plate 32 may be provided with the enlarged head 64, 116 of the screw(s) 34, 104 predisposed within the channels 60 and/or apertures 62 of the bone plate 32 such that the plate 32 is secured in position against the vertebrae as the screws 34, 104 are tightened. Alternately, the screws 34, 104 may be provided separately from the bone plate 32 and then assembled into the plate 32 during the procedure. In order to assist the surgeon in such an assembly procedure, an assembly tool 160 such as is shown in FIG. 17 may be provided. The tool 160 includes a guide block 162 disposed on a manipulation arm 164. The manipulation arm 164 preferably includes a handle 166 for the surgeon's comfort during the placement procedure.

In order to facilitate insertion of screw(s) 34, 104 through the plate and into the desired bone, the guide block 162 of the tool 160 includes one or more bores 168 that extend through a portion of the guide block 162, here from the top surface 170 to the bottom surface 171 of the guide block 162. During the placement procedure, the surgeon places the bone plate 32 in the desired location and then positions the guide block 162 along the upper surface of the plate 32 with the bore(s) 168 positioned adjacent a channel 60 or aperture 62. The surgeon may then insert a screw 34, 104 through the bore 168 (holding the screw with the tool 130 or otherwise), and rotates the screw 34, 104 into the target. Those of skill in the art will appreciate that the bore 168 of the guide block 162 guides the screw 34, 104 for straight axial movement.

As shown in FIG. 18, the bore 168 of guide block 162 of the tool 160 of FIG. 17 includes a pair of bores 172, 174 that include relatively separate proximal ends 176, 178, and a shared distal end 180. In this way, in addition to positioning the guide block 162 itself at the desired angle to provide the optimal screw placement, the surgeon may utilize one or the other of the pair of bores 172, 174 to place the screw 34, 104 at a desired angle through the bone plate 32.

While the guide block 162 of the tool 106 of FIGS. 17 and 18 includes two pairs of dual bores 172, 174, the guide block may have alternate construction. For example, one or both of the bores 182 of the guide block 184 may each have a single axis 186, such as shown in FIG. 19, wherein two such bores 182 are provided. Alternately, the guide block 188 may include a single bore 190 with dual axes or with a single axis 192, such as is shown, for example, in FIG. 20. The guide blocks shown are by way of example only. It will be appreciated by those of skill in the art that the guide block may comprise alternate numbers and/or combinations of bores and/or constructions of bores in keeping with the invention. Moreover, one or more such guide blocks 162, 184, 188 may be provided as part of a tool kit that further includes the manipulation arm 164. The desired block 162, 184, 188 may be selectively coupled to the end of the manipulation arm 164 by way of a screw, pin, or the like 194 extending through a bore 196.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An anchor device for securing to a bone a plate having an upper surface and a lower surface and apertures extending from the upper surface to the lower surface, the apertures having inside concave edge walls spaced apart a given inner diameter and having an upper surface opening and a lower surface opening, each having a diameter smaller than the inner diameter, comprising:

a screw including a head portion and a threaded shank with a distal tip and a central longitudinal axis, the head portion having a central opening exposed at the proximal end of the screw and an annular wall around the central opening, the annular wall having an inner and an outer surface, the outer surface having a relaxed outer diameter substantially equal to the inner diameter of the aperture, and the annular wall having a plurality of slots that separate the annular wall into a plurality of petals, wherein the inner surface of the annular wall includes a plurality of shallow recesses and a plurality of deep recesses, wherein at least one of the petals has an inner surface of the annular wall having at least two of the shallow recesses, the screw further including an internal surface of defined shape originating in the central opening for engagement by a matingly-configured screw driving tool for driving the screw into the bone; and a locking disc rotatably disposed within the central opening and having a periphery of defining a plurality of extending protrusions, the locking disc rotatable between a first rotational position and second rotational position;

wherein the shallow recesses, the deep recesses, and the protrusions are configured so that when the locking disc is in the first rotational position, the protrusions are disposed in the deep recesses in the inner surface of the annular wall with a clearance permitting the petals to flex inwardly to insert the screw head into the aperture past the upper surface opening, and when the locking disc is rotated to the second rotational position two of the protrusions are disposed in and engage with a corresponding two of the shallow recesses formed on the inner surface of at least one of the petals to establish a corresponding two engagements when the petal substantially is at its free relaxed state to prevent the petal from flexing inwardly, whereby the head is selectively captured within the concave edge walls of the plate aperture.

2. The device of claim 1, wherein the screw's internal surface comprises a bore extending distally from the central opening along the central longitudinal axis of the shank.

3. The device of claim 2, wherein the locking disc has a central aperture that surrounds the bore, thereby permitting access to the bore by the screw driving tool.

4. The device of claim 2, wherein the bore has a hexagonal cross-section.

5. The device of claim 2, wherein the bore has a cross-sectional shape selected from among the following: slotted, triangular, square, rectangular, pentagonal or octagonal.

6. The device of claim 1, wherein the plurality of slots comprises four slots and the plurality of petals comprises four petals, and wherein the periphery of the locking disc defines eight protrusions.

7. The device of claim 6, wherein at the first rotational position of the locking disc each of a first four of the eight protrusions is aligned with and engaged within a corresponding one of the four deep recesses that are aligned with the four slots, and each of a second four of the eight protrusions is aligned with and engaged within a corresponding one of the four deep recesses.

8. The device of claim 1, wherein the number of shallow recesses and the number of deep recesses are each equal to the number of protrusions.

9. The device of claim 1, wherein the locking disc includes at least a pair of proximally opening notches configured for engagement by a tool to effectuate rotation of the disc from the first rotational position to the second rotational position.

10. The device of claim 1, wherein the distal tip of the screw is self-tapping.

11. The device of claim 1, wherein the locking disc, at the first and at the second of the rotational positions, is fully nested within the central opening and does not protrude beyond the proximal end of the screw.

12. The device of claim 1, wherein the number of shallow recesses is equal to the number of deep recesses, and the shallow recesses and the deep recesses are arranged in an alternating pattern along the inner surface of the annular wall.

13. The device of claim 12, wherein the inner surface of each of said petals has two shallow recesses and has one deep recess between the two shallow recesses.

14. The device of claim 13, wherein the shallow recesses are equally spaced.

15. The device of claim 14, wherein the slots are formed so that the petals have a common width and are equally spaced.

16. The device of claim 15, wherein the inner surface of the annular wall includes one of the deep recesses aligned with each of the slots.

17. The device of claim 1, wherein the shallow recesses are equally spaced.

18. The device of claim 1, wherein the slots are formed so that the petals have a common width and are equally spaced.

19. The device of claim 1, wherein the inner surface of the annular wall includes one of the deep recesses aligned with each of the slots.

20. A system for securing a bone to a plate having an upper surface and a lower surface and apertures extending from the upper surface to the lower surface, the apertures having inside concave edge walls spaced apart a given inner diameter and having an upper surface opening and a lower surface opening, each having a diameter smaller than the inner diameter, comprising:

a screw including a head portion and a threaded shank with a distal tip and a central longitudinal axis, the head portion having a central opening exposed at the proximal end of the screw and an annular wall around the central opening, the annular wall having an inner and an outer surface, the outer surface having a relaxed outer diameter substantially equal to the inner diameter of the aperture and having a plurality of slots that separate the annular wall into a plurality of petals, wherein the inner surface of the annular wall includes a plurality of shallow recesses and a corresponding plurality of deep recesses, wherein at least one of the petals has an inner surface of the annular wall having at least two of the shallow recesses, the screw further including an internal surface of defined shape originating in the central opening for engagement by a matingly-configured screw driving tool for driving the screw into the bone; and a locking disc rotatably disposed within the central opening and having a periphery of defining a plurality of extending protrusions, the locking disc rotatable between a first rotational position and second rotational position, the locking disc having a central aperture that surrounds the internal bore of the screw to permit access to the internal bore, and at least a pair of proximally opening notches configured for engagement to effectuate rotation of the disc; and a tool with a handle, a shaft extending from the handle and having a distal end configured to mate with the internal bore of the screw to permit selective rotation of the screw, and a sleeve member axially slideable along and rotatable about the shaft and having a distal end with structure that mates with the pair of proximally opening notches in the locking disc to permit selective rotation of the disc;

wherein the shallow recesses, the deep recesses, and the protrusions are configured so that when the locking disc is in the first rotational position, the protrusions are disposed in the deep recesses with a clearance permitting the petals to flex inwardly to insert the screw head into the aperture past the upper surface opening, and when the locking disc is rotated to the second rotational position two of the protrusions are disposed in and engage with a corresponding two of the shallow recesses formed on the inner surface of at least one of the petals, to establish a corresponding two engagements with the petal substantially at its free relaxed state, to prevent the petal from flexing inwardly, whereby the head is selectively captured within the concave edge walls of the plate aperture.

21. The system of claim 20, wherein the internal bore has a hexagonal cross-section and the distal end of the tool shaft has a mating hexagonal configuration.

22. The system of claim 20, wherein the internal bore has a cross-sectional shape selected from among slotted, triangular, square, rectangular, pentagonal or octagonal, and the distal end of the tool shaft has a correspondingly mated configuration.

23. The system of claim 20, wherein the plurality of slots comprises four slots and the plurality of petals comprises four petals, and wherein the periphery of the locking disc defines eight protrusions.

24. The device of claim 23, wherein at the first rotational position of the locking disc each of a first four of the eight protrusions is aligned with and engaged within a corresponding one of the four deep recesses that are aligned with the four slots, and each of a second four of the eight protrusions is aligned with and engaged within a corresponding one of the four deep recesses.

25. The system of claim 20, wherein the number of protrusions is twice the number of petals, and the protrusions are configured with respect to the shallow recesses such that upon rotation of the locking disc to the second rotational position at least two protrusions engage a corresponding at least of the two shallow recesses on the inside surface of each petal.

26. The system of claim 20, wherein the locking disc, at the first and at the second of the rotational positions, is fully nested within the central opening and does not protrude beyond the proximal end of the screw.

27. The system of claim 20, wherein the sleeve of the tool further includes a flange member, whereby, when the distal ends of the shaft and the sleeve are engaged, respectively, with the screw and the locking disc, a user may maintain the rotational position of the screw by grasping the tool handle and simultaneously rotate the flange and the sleeve and thus also the disc.

28. The system of claim 20, further comprising a screw aligning device having a guide block and a manipulation arm, the guide block including at least one bore through which the screw can pass and which holds the screw in a desired angular position as it is being driven into the bone.

29. The system of claim 20, wherein the number of shallow recesses is equal to the number of deep recesses, and the shallow recesses and the deep recesses are arranged in an alternating pattern along the inner surface of the annular wall.

30. The system of claim 29, wherein the inner surface of each of said petals has two shallow recesses and has one deep recess between the two shallow recesses.

31. The system of claim 30, wherein the shallow recesses are equally spaced.

32. The system of claim 31, wherein the slots are formed so that the petals have a common width and are equally spaced.

33. The system of claim 32, wherein the inner surface of the annular wall includes one of the deep recesses aligned with each of the slots.

34. The system of claim 20, wherein the inner surface of each of said petals has two shallow recesses and has one deep recess between the two shallow recesses.

35. The system of claim 20, wherein the shallow recesses are equally spaced.

36. The system of claim 20, wherein the slots are formed so that the petals have a common width and are equally spaced.

37. The system of claim 20, wherein the inner surface of the annular wall includes one of the deep recesses aligned with each of the slots.

38. A method of securing to a bone a plate having an upper surface and a lower surface and apertures extending from the upper surface to the lower surface, the apertures having inside concave edge walls spaced apart a given inner diameter and having an upper surface opening and a lower surface opening, each having a diameter smaller than the inner diameter, comprising:
positioning a selected aperture of the plate adjacent a desired location on the bone;
aligning a bone screw through the selected aperture and into contact with the bone at a desired angular orientation, the screw including
a threaded shank with a distal tip,
a head portion having a central opening exposed at the proximal end of the screw and an annular wall around the central opening, the annular wall having an inner and an outer surface, the outer surface having a relaxed outer diameter substantially equal to the inner diameter of the aperture and having a plurality of slots that separate the annular wall into a plurality of petals, wherein the inner surface of the annular wall includes a plurality of spaced shallow recesses and a plurality of deep recesses, wherein at least one of the petals has at least two of the shallow recesses,
an internal bore of defined shape originating in the central opening for engagement by a driving tool, and
a locking disc rotatably disposed within the central opening and having a periphery of defining a plurality of extending protrusions, the locking disc rotatable between a first rotational position and a second rotational position, the locking disc having a central aperture that surrounds the internal bore of the screw to permit access to the internal bore, and at least a pair of proximally opening notches configured for engagement to effectuate rotation of the disc, wherein the shallow recesses, the deep recesses, and the protrusions are configured so that when the locking disc is in the first rotational position at least one of the petals is flexible inwardly to permit inserting the screw head into the aperture past the upper surface opening, and when the locking disc is rotated to the second rotational position the two of the protrusions are disposed in and engage with a corresponding two of the shallow recesses formed on the inner surface of at least one of the petals, with the petal substantially at its free relaxed state, to establish a corresponding two engagements to prevent the petal from flexing inwardly;
engaging the internal bore of the screw with a driving tool having a handle and a shaft with a distal end configured to mate with the internal bore, driving the distal tip of the screw against the bone and selectively rotating the screw until it penetrates the bone to a desired depth, the driving tool further including
a sleeve member axially slideable along and rotatable about the shaft, the sleeve member including a flange for effectuating movement of the sleeve relative to the shaft, and a distal end with structure that mates with the pair of proximally opening notches in the locking disc; and
manipulating the flange first to slide the sleeve into mating engagement with the pair of proximally opening notches in the locking disc and second to rotate the locking disc from the first rotational position to the second rotational position, whereupon the head is captured by the concave wall edges of the plate aperture.

39. The method of claim 38, further comprising the step of simultaneously maintaining the rotational position of the screw by grasping the tool handle while manipulating the flange to effectuate rotation of the locking disc.

40. The method of claim 38, further comprising the step of employing a screw aligning device having a guide block and a manipulation arm, the guide block including at least one bore through which the screw can pass and which maintains the screw in the desired angular orientation as it is being driven into the bone.

41. The method of claim 38, wherein the step of engaging the internal bore of the screw with a driving tool having a handle and a shaft with a distal end configured to mate with the internal bore, driving the distal tip of the screw against the bone and selectively rotating the screw further comprises rotating the locking disc to the first position, and wherein the selectively rotating the screw until it penetrates the bone to a desired depth includes rotating the screw until screw head the screw head is in the aperture, past the upper aperture opening, by the rotating urging the outer surface of the petals against the upper surface aperture opening to flex the petals inward and continuing urging the screw head until the petals pass the upper surface aperture opening and return to the free, relaxed state within the concave wall edges of the aperture.

42. The method of claim 38, wherein the number of shallow recesses is equal to the number of deep recesses, and the shallow recesses and the deep recesses are arranged in an alternating pattern along the inner surface of the annular wall.

43. The method of claim 42, wherein the inner surface of each of said petals has two shallow recesses and has one deep recess between the two shallow recesses.

44. The method of claim 43, wherein the shallow recesses are equally spaced.

45. The method of claim 44, wherein the slots are formed so that the petals have a common width and are equally spaced.

46. The method of claim 45, wherein the inner surface of the annular wall includes one of the deep recesses aligned with each of the slots.

47. The method of claim 38, wherein the inner surface of each of said petals has two shallow recesses and has one deep recess between the two shallow recesses.

48. The method of claim 38, wherein the shallow recesses are equally spaced.

49. The method of claim 38, wherein the slots are formed so that the petals have a common width and are equally spaced.

50. The method of claim 38, wherein the inner surface of the annular wall includes one of the deep recesses aligned with each of the slots.

51. A bone plate system, comprising:
 a plate having an upper surface and a lower surface and an aperture extending from the upper surface to the lower surface, the aperture having inside concave edge walls spaced apart a given inner diameter and having an upper surface opening and a lower surface opening, each having a diameter smaller than the inner diameter;
 a screw including a head portion at a proximal end and a threaded shank with a distal tip, the head portion having a mating structure exposed through a central opening at the proximal end, for engaging a matingly-configured screw driving tool for driving the screw, and having an annular wall around the central opening, the annular wall having an inner and an outer surface, the inner surface including a plurality of shallow recesses and a plurality of deep recesses, the annular wall having a plurality of slots that separate the annular wall into a plurality of petals such that each petal has a portion of the inner surface having at least two of the shallow recesses, the outer surface having a relaxed outer diameter substantially equal to the inner diameter of the aperture and; and
 a locking disc rotatable within the central opening and having a periphery defining a plurality of protrusions, each protrusion having a high point configured for selective engagement within one of the shallow and one of the deep recesses,
 wherein the shallow recesses, the deep recesses, and the protrusions are configured so that when the locking disc is in a first rotational position, the protrusions engage with the deep recesses in the inner surface of the annular wall with a clearance to enable inward flex of the petals of the screw head sufficient for insertion through the upper surface aperture opening into the aperture, and when the locking disc is in a second rotational position, the respective high point of least two of the protrusions engage with a corresponding at least two of the shallow recesses formed on the inner surface of each of the petals, to establish a corresponding two engagements preventing the petals from flexing inwardly, thereby preventing the screw head from being compressed sufficiently to pass through the upper aperture opening, thereby providing for capturing the head within the concave edge walls of the plate aperture.

52. The bone plate system of claim 51, wherein the number of shallow recesses is equal to the number of deep recesses, and the shallow recesses and the deep recesses are arranged in an alternating pattern along the inner surface of the annular wall.

53. The bone plate system of claim 52, wherein the inner surface of each of said petals has two shallow recesses and has one deep recess between the two shallow recesses.

54. The bone plate system of claim 51, wherein at least one of said apertures of at least one of said plates is an elongated slot aperture, the elongated aperture having a width equal to said inner diameter, and having an upper surface elongated aperture opening and a lower surface elongated aperture opening, the upper surface elongated aperture opening having a width smaller than the inner diameter and the lower surface elongated aperture opening having a width smaller than the inner diameter, and wherein at least one of the screws has its plurality of petals configured so that when its locking disc is rotated to the second rotational position the screw head of said screw is captured by the elongated slot aperture and, concurrent with said capture, the screw head is movable along a length of the elongated slot aperture.

55. The bone plate system of claim 51,
 wherein the annular wall includes four slots separating the annular wall into four petals,
 wherein the locking disc includes eight protrusions, and
 wherein at the first rotational position of the locking disc each of a first four of the eight protrusions is aligned with and engaged within a corresponding one of the four deep recesses that are aligned with the four slots, and each of a second four of the eight protrusions is aligned with and engaged within a corresponding one of the four deep recesses.

56. The bone plate system of claim 55, wherein at the second rotational position of the locking disc each of the eight protrusions is aligned with and engaged within a corresponding one of the two shallow recesses.

\* \* \* \* \*